(12) United States Patent
Hanks et al.

(10) Patent No.: US 12,097,011 B1
(45) Date of Patent: Sep. 24, 2024

(54) WEARABLE PATCH DEVICE FOR CORE BODY TEMPERATURE MEASUREMENTS

(71) Applicants: John Hanks, Austin, TX (US); Amir Tofighi Zavareh, College Station, TX (US); Limei Tian, College Station, TX (US)

(72) Inventors: John Hanks, Austin, TX (US); Amir Tofighi Zavareh, College Station, TX (US); Limei Tian, College Station, TX (US)

( * ) Notice: Subject to any disclaimer, the term of this patent is extended or adjusted under 35 U.S.C. 154(b) by 0 days.

(21) Appl. No.: 18/517,879

(22) Filed: Nov. 22, 2023

Related U.S. Application Data

(63) Continuation of application No. 18/487,268, filed on Oct. 16, 2023.

(60) Provisional application No. 63/496,758, filed on Apr. 18, 2023.

(51) Int. Cl.
| | |
|---|---|
| *A61B 5/01* | (2006.01) |
| *A61B 5/00* | (2006.01) |
| *G01K 13/20* | (2021.01) |
| *G06N 20/00* | (2019.01) |
| *G16H 50/20* | (2018.01) |

(52) U.S. Cl.
CPC ............. *A61B 5/01* (2013.01); *A61B 5/6833* (2013.01); *A61B 5/7275* (2013.01); *G06N 20/00* (2019.01); *G16H 50/20* (2018.01); *A61B 2560/0252* (2013.01); *A61B 2560/0285* (2013.01); *A61B 2560/0462* (2013.01); *A61B 2562/0271* (2013.01); *A61B 2562/046* (2013.01); *A61B 2562/125* (2013.01); *A61B 2562/164* (2013.01); *G01K 13/20* (2021.01)

(58) Field of Classification Search
CPC ....... A61B 5/01; A61B 5/6833; A61B 5/7275; A61B 2560/0252; A61B 2560/0285; A61B 2560/0462; A61B 2562/0271; A61B 2562/046; A61B 2562/125; A61B 2562/164; G16H 50/20; G01K 13/20
See application file for complete search history.

(56) References Cited

U.S. PATENT DOCUMENTS

| | | | |
|---|---|---|---|
| 2021/0100454 A1* | 4/2021 | Gannon | A61B 5/746 |
| 2021/0290072 A1* | 9/2021 | Forrest | A61B 5/6823 |

* cited by examiner

*Primary Examiner* — Devin B Henson
*Assistant Examiner* — Evelyn Grace Park
(74) *Attorney, Agent, or Firm* — Benjamin Aaron Adler

(57) ABSTRACT

Provided herein are thermal devices and single-use temperature measurement devices to predict and to monitor core body temperature in a subject, such as a patient. The devices utilize a plurality of thermal or temperature sensors disposed on a patch and insulated one from the other and a connection to a machine learning algorithm for prediction and monitoring. Also provided are systems and methods using the thermal device or temperature monitoring device and the machine learning algorithm to predict and measure core body temperature in the subject.

19 Claims, 16 Drawing Sheets

▪ Tcore prediction
▪ Measured Tcore

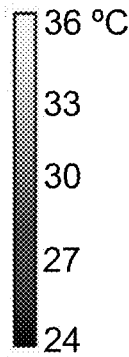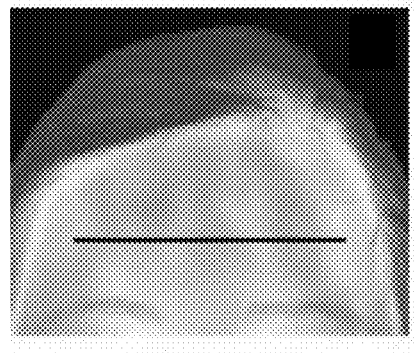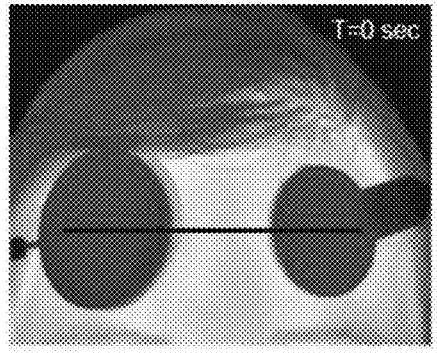
FIG. 5A      FIG. 5B
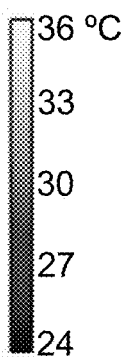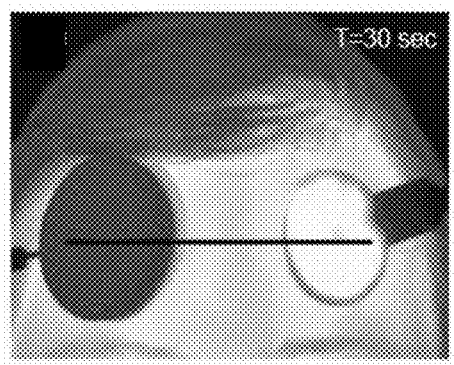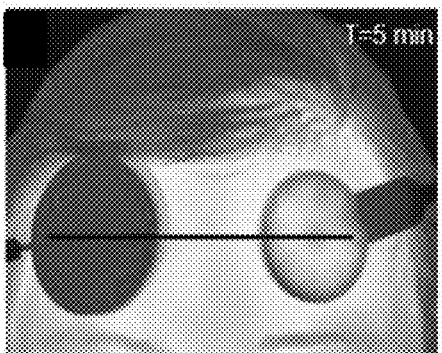
FIG. 5C      FIG. 5D

WEARABLE PATCH DEVICE FOR CORE BODY TEMPERATURE MEASUREMENTS

CROSS-REFERENCE TO RELATED APPLICATIONS

This application is a continuation under 35 U.S.C. § 120 of pending non-provisional application U.S. Ser. No. 18/487,268, filed Oct. 16, 2023, which claims benefit of priority under 35 U.S.C. § 119(e) of provisional application U.S. Ser. No. 63/496,758, filed Apr. 18, 2023, the entirety of which is hereby incorporated by reference.

BACKGROUND OF THE INVENTION

Field of the Invention

The present invention relates to the field of medical devices and diagnosis. More particularly, the present invention relates to a wearable wireless medical device to predict core body temperature of a subject.

Cross-Reference to Related Art

Core body temperature (CBT) is the temperature of the internal organs of the body. While core body temperature is tightly regulated around 37° C., skin temperature highly depends on environmental factors (1). Monitoring core body temperature provides important insight into the health and disease conditions of individuals (2,3). If the core body temperature of individuals falls out of the temperature range of 36-38° C., hypothermia or hyperthermia occurs which needs timely clinical intervention. Hyperthermia occurs when the core body temperature is above the normal threshold of 38° C. and can lead to fluid loss and an increase in metabolic rate, oxygen consumption, and cardiac output (4,5). Hyperthermia also can be fatal, such as during a heat stroke, as it could result in a core body temperature above 40° C., disseminated intravascular coagulation, hypotension, tachycardia, and hyperventilation (5). Hypothermia occurs when the core body temperature is below the temperature limit of 36° C. (6). During pharmaceutical and surgical procedures, hypothermia can result from increased heat loss, decreased metabolic rate, and impaired thermoregulation (4,6). Hypothermia conditions cause significant metabolic, functional, and morphologic alterations in vital organs, such as cardiac irritability, impairment of coagulation cascade and platelet functioning, and respiratory secretion retention (4,7).

Current core body temperature monitoring techniques include medical devices applied at the nasopharyngeal, esophageal, or pulmonary artery sites (8-10). These devices are highly invasive and limited to applications in operating rooms. They are not suitable for long-term continuous monitoring of patients and healthy individuals. To address such limitations, noninvasive methods of measuring core body temperature through the temporal artery were sought to provide more accuracy compared to axillary and ear measurements (6,11). Existing wearable noninvasive approaches to quantify core body temperature primarily rely on heat flux measurements (6,12).

For example, the 3M zero-heat-flux (ZHF) device is a noninvasive core body temperature monitoring system that comprises a heater and two thermometers separated by an insulator and a connector to a power outlet for heater and sensor operation (13). The heater eliminates the thermal gradient between the skin and the heater, extending the same temperature from the core to the skin and further to the heater element. During perioperative settings, the ZHF devices were clinically proven to measure CBT as accurately as the invasive esophageal and nasopharyngeal techniques (14). In perioperative settings, the mean CBT bias was found to be 0.03° C. with population limits of agreement between −0.93° C. and 0.98° C. (6). However, the ZHF device requires a connection to an electrical outlet and is not suitable to use in resource-limited settings.

Another approach to quantify CBT is based on measured heat flux using two temperature sensors without the heater, which consumes less power and enables wireless operation (15). However, previous reports showed that the heater-free devices predicted the core body temperature lower than the ZHF devices (12). The 95% limits of agreement between the two devices exceeded 0.5° C., a normal temperature fluctuation range (16,17), therefore not satisfactory. Multiple temperature sensors, for example, 4-8, have been reported to enhance the accuracy (18,19). For example, a miniaturized core body temperature monitoring system based on dual heat flux relies on the temperature difference between the thermometers less than 0.5° C. (18). However, the accuracy of the miniaturized off-the-shelf thermometers 0.1° C., resulting a high uncertainty. Another method relies on solving closed form theoretical equations that require the hard-to-measure parameters, such as tissue thermal conductivity and thickness (19). In addition, those sensors were not constructed within single wearable devices and the performance in human subjects was not validated.

Thus, there is a need in the art for low power, devices that wirelessly integrate with algorithms to quantify and monitor core body temperature of a subject. Particularly, the prior art is deficient in wearable thermal devices that wirelessly integrate with machine learning algorithms to accurately quantify core body temperature. The present invention fulfills this long-standing need and desire in the art.

SUMMARY OF THE INVENTION

The present invention is direct to a thermal device for monitoring core body temperature in a subject. The thermal device comprises a patch made of a flexible, folded substrate that when folded forms a top layer that is a thermal zone and a bottom layer having an adhesive disposed thereon where the patch is removably attachable to the skin. The patch has on the thermal zone an annular copper ring circumferentially disposed around a thermally conducting material and electrically isolated therefrom, a pair of copper semi-circular components disposed within the annular copper ring and electrically isolated therewithin, where the thermally conducting material is disposed beneath the pair of copper semi-circular components, a thermal sensing component comprising a plurality of thermal sensors disposed within the thermal zone on the top layer and operably connected thereon, and a first insulating material disposed in a covering relationship on the top layer of the patch. A second insulating material is disposed in a covering relationship on the bottom layer of the patch and comprises a central opening therethrough sized to secure the thermally conducting material therein. The device comprises means for communicating data acquired via the thermal sensing component to a machine learning algorithm configured to predict the core body temperature in the subject.

The present invention also is directed to a system for predicting core body temperature in a subject. The system comprises the patch as described herein and a machine learning algorithm tangibly stored on an electronic device having at least a memory and a processor. The machine learning algorithm is configured to receive input from at least the plurality of thermal sensors disposed on the patch and to output at least the predicted core body temperature.

The present invention is directed to a related system that further comprises at least one environmental context sensor configured to provide contextual information where the machine learning algorithm is configured to wirelessly receive input therefrom.

The present invention is directed further to a method for predicting a core body temperature of a patient in need thereof. In the method in step a), the patch comprising the system described herein is adhered via the adhesive disposed thereon to the forehead of the patient. In step b), the data acquired by the plurality of thermal sensors is transmitted as input into the machine learning algorithm comprising the system over a period of time, in step c) is analyzed to predict the core body temperature, and in step d) the core body temperature is outputted.

The present invention is directed to a related method further comprising in step e) transmitting into the machine learning algorithm contextual data acquired by at least one environmental contextual sensor.

The present invention is directed to another related method further comprising repeating steps b) to e) at least once over a period of about 24 hours.

The present invention is directed further still to a single-use temperature measurement device for measuring core body temperature of a subject. The single-use temperature measurement device has a flexible, folded substrate comprising a thermal zone on a top surface thereof. An electrically isolated annular copper ring is disposed on the top surface of the flexible, folded substrate to surround the thermal zone and a first semi-circular copper component and a second semi-circular copper component are both disposed on the top surface of the flexible, folded substrate inside the electrically isolated annular copper ring and both are electrically isolated therewithin. A plurality of temperature sensors are disposed within the thermal zone on the flexible, folded substrate and are operably connected thereto. A top insulator is disposed over the top surface of the flexible, folded substrate and a bottom flexible insulator is formed with a central opening therethrough and disposed on a bottom surface of the flexible, folded substrate to cover sections thereon formed by the plurality of temperature sensors. A thermal plug is disposed beneath the first semi-circular copper component and the second semi-circular copper component and within the central opening through the bottom flexible insulator. An adhesive is disposed on the bottom surface of the flexible, folded substrate to removably secure to the subject. The single-use temperature measurement device has means for connecting to a machine learning algorithm.

The present invention is directed further still to a system for measuring core body temperature in a subject. The system comprises the single-use temperature measurement device as described herein. A machine learning algorithm is tangibly stored on an electronic device having at least a memory and a processor. The machine learning algorithm is configured to receive and analyze input data from the plurality of temperature sensors disposed on the temperature measurement device and from an environmental context sensor and to output at least the predicted core body temperature.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1A is a schematic illustration of the main functional components in the thermal device 100 illustrating an exploded view of a patch 110 of a flexible, foldable substrate that upon folding has a top layer or top surface 110a that is a thermal zone, a bottom layer or bottom surface 110b comprising a flexible insulator or flexible insulating foam 120 with a thermally conducting material or thermal plug 130 disposed in the middle thereof, an annular copper ring 140 and a pair of semi-circular copper components 150a,b, temperature sensors or thermal sensors (T1-T4) 160a,b,c,d disposed within the thermal zone, means 170 for communicating with a machine learning algorithm 200 (see FIG. 8C), an adhesive 180 disposed on the bottom layer and a top insulator or insulating foam 190 that covers or encapsulates the top layer. FIG. 1B is an optical image of the flexible substrate with the four temperature sensors. FIGS. 1C-1D are the top view and side view, respectively, of the optical images of the flexible substrate assembled with the thermal plug and insulating foam.

FIGS. 2A-2C show the temporal changes of T1-T4 in the thermal device with the thermal plug of varying thermal conductivities of 0.05 W/mK, 0.34 W/mK, and 0.70 W/mK. FIG. 2D shows the steady state temperatures of T1-T4 under varying ambient temperatures of 18° C.-27° C. FIGS. 2E-2F are respective top view temperature distribution of the thermal devices with Cu pattern and without Cu pattern on the substrate. FIG. 2G is a temperature profile along the line denoted in FIG. 2E and FIG. 2F.

FIG. 3A shows the layers of the tissue phantom. FIG. 3B is a cross-section schematic of the experimental setup highlighting the sensor out-of-plane locations. FIG. 3C shows that T1-T4 changes with the increase in the simulated Tcore. FIG. 3D shows a regression calibration of Tcore using T1-T4. FIGS. 3E-3F show the T core prediction using the calibrated regression model and the corresponding prediction error, respectively.

FIGS. 5A-5G illustrate device testing on human subjects. Thermal images are shown of the forehead before the devices applied (FIG. 5A), after the devices applied (FIG. 5B), after the ZHF device activation for 30 seconds (FIG. 5C), and after the ZHF device activation for 5 minutes (FIG. 5E). FIG. 5F shows temperature profiles along the lines denoted in FIGS. 5A-5D. T1-T4 and Tcore changes with time are shown after applying the devices on a female forehead (FIG. 5F) and a male forehead (FIG. 5G).

FIG. 8C is a flow diagram 200 of calibration and validation of the nonlinear machine learning algorithms used in vivo.

DETAILED DESCRIPTION OF THE INVENTION

Figure 1A:
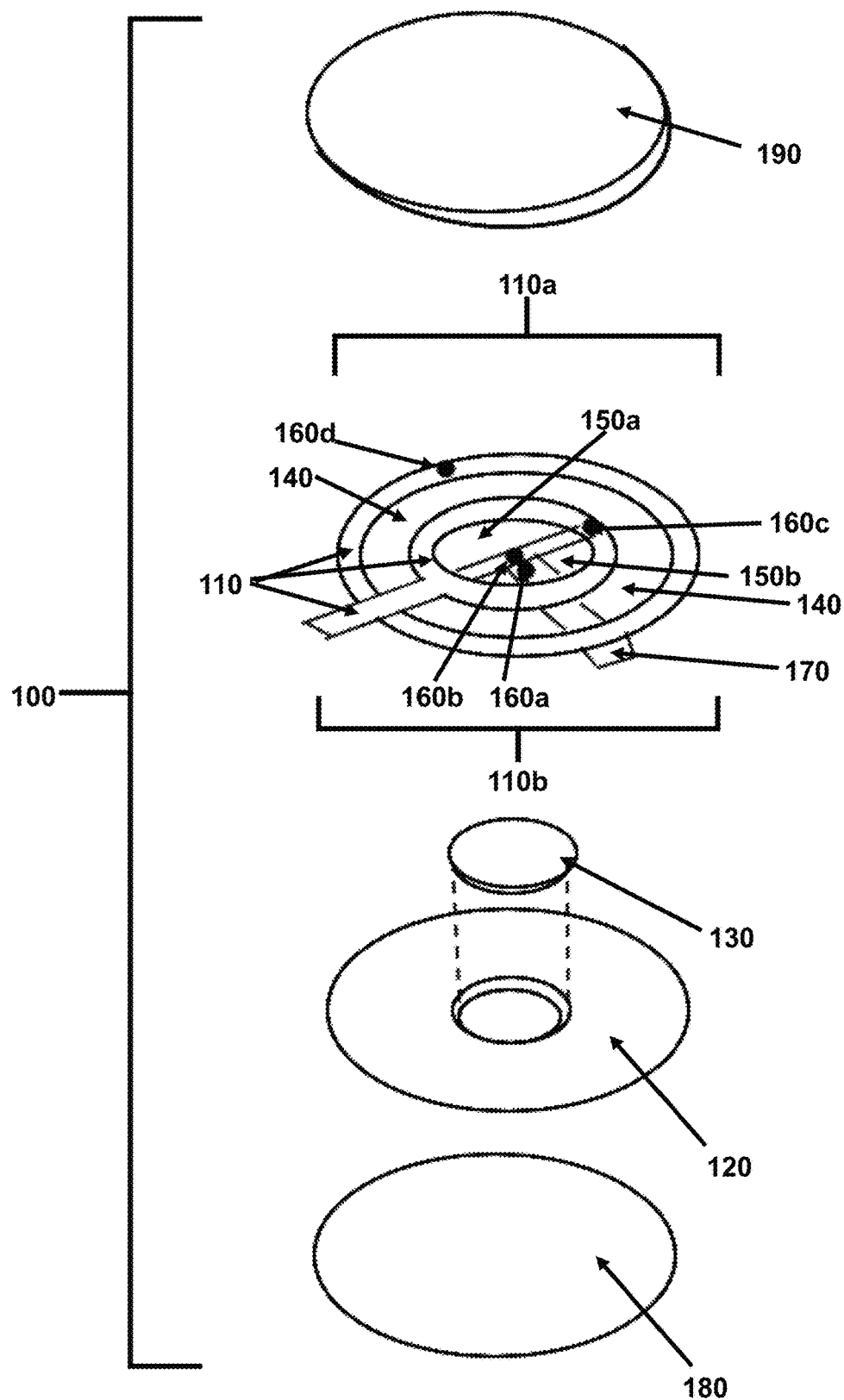
FIGS. 1A-1D illustrate the wearable device design for core body temperature monitoring.

As used herein, the articles "a" and "an" when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, components, method steps, and/or methods of the invention.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the terms "comprise" and "comprising" are used in the inclusive, open sense, meaning that additional elements may be included.

As used herein, the terms "consists of" and "consisting of" are used in the exclusive, closed sense, meaning that additional elements may not be included.

As used herein, the term "includes" or "including" is used herein to mean "including, but not limited to". The terms "includes", "including" and "including but not limited to" are used interchangeably.

As used herein, the term "about" refers to a numeric value, including, for example, whole numbers, fractions, and percentages, whether or not explicitly indicated. The term "about" generally refers to a range of numerical values (e.g., +5-10% of the recited value) that one of ordinary skill in the art would consider equivalent to the recited value (e.g., having the same function or result). In some instances, the term "about" may include numerical values that are rounded to the nearest significant figure.

As used herein, the ordinal adjectives "first", "second", "third", and "fourth" unless otherwise specified are used to describe a common object, merely indicate that different instances of like objects are being referred to, and are not intended to imply that the objects so described must be in a given sequence, either temporally, spatially, in ranking, or in any other manner.

As used herein, the term "subject" refers to a human subject or other mammal.

As used herein, the terms "thermal sensors" and "temperature sensors" are interchangeable as are the terms "de.

As used herein, the terms "insulator", "insulating material" and "insulation" are interchangeable.

As used herein, the term "electronic device" refers to any smart device that wirelessly and interactively connects to other devices or networks and has properties of machine learning, for example, but not limited to, a computer, a tablet, or a smartphone.

In one embodiment of the present invention there is provided thermal device for monitoring core body temperature in a subject, comprising a patch made of a flexible, foldable substrate that when folded forms a top layer that is a thermal zone and a bottom layer having an adhesive disposed thereon, where the patch is removably attachable to the skin.

In this embodiment the patch comprises, on the thermal zone, an annular copper ring circumferentially disposed around a thermally conducting material and electrically isolated therefrom; a pair of copper semi-circular components disposed within the annular copper ring and electrically isolated therewithin; where the thermally conducting material is disposed beneath the pair of copper semi-circular components; a thermal sensing component comprising a plurality of thermal sensors disposed within the thermal zone on the top layer and operably connected thereon; and a first insulating material disposed in a covering relationship on the top layer of the patch; a second insulating material disposed in a covering relationship on the bottom layer of the patch and comprising a central opening therethrough sized to secure the thermally conducting material therein; and means for communicating data acquired via the thermal sensing component to a machine learning algorithm configured to predict the core body temperature in the subject. In this embodiment the thermally conducting material may be a low-density polyethylene formed as a thermal plug.

Also in this embodiment the plurality of thermal sensors may comprises a first thermal sensor disposed between the pair of copper semi-circular components; a second thermal sensor disposed on the flexible, folded substrate radially beyond the edge of the annular copper ring; a third thermal sensor disposed on the flexible, folded substrate between the annular copper ring and the pair of copper semi-circular components or disposed on the annular copper ring; and a fourth thermal sensor disposed in a section of the flexible, folded substrate proximate to the first thermal sensor.

In addition, in this embodiment the first insulating material may be a thermal insulating foam and the second insulating material on the bottom layer may be a flexible insulating foam disposed to cover sections formed by the plurality of thermal sensors to define a thermal spatial gradient across the patch.

In another embodiment of this invention there is provided a system for predicting core body temperature in a subject, comprising the patch as described supra; and the machine learning algorithm tangibly stored on an electronic device having at least a memory and a processor, where the machine learning algorithm is configured to receive input from at least a plurality of thermal sensors contained on the thermal component disposed on the patch and to output at least the predicted core body temperature.

Further to this embodiment, the system comprises at least one environmental context sensor configured to provide contextual information, where the machine learning algorithm is configured to receive input therefrom. In an aspect of this further embodiment the input from the at least one environmental contextual sensor may comprise room temperature or ambient air velocity or a combination thereof. In another aspect of this embodiment, the input from the at least one environmental context sensor may further comprise an indication that the patch is covered or is uncovered after placement on the subject. In yet another aspect, the input from the at least one environmental contextual sensor may further comprise at least one of the sex of the patient, a body mass index or time of a menstrual cycle.

In yet another embodiment of this invention there is provided a method for predicting a core body temperature of a patient in need thereof, comprising a) adhering the patch comprising the system as described supra via the adhesive disposed thereon to the forehead of the patient; b) transmitting data acquired by the plurality of thermal sensors as input into the machine learning algorithm comprising the system over a period of time; c) analyzing the data to predict the core body temperature; and d) outputting the core body temperature.

Further to this embodiment, the method comprises e) transmitting into the machine learning algorithm contextual data acquired by at least one environmental contextual sensor. Further to both embodiments the method comprises repeating steps b) to e) at least once over a period of about 24 hours. In these further embodiments, the contextual data is ambient data that may comprise room temperature or ambient air velocity or is patient data that may comprise sex, body mass index or time of a menstrual cycle or a combination of the ambient data and the patient data. Also, in these further embodiments, the contextual data may further comprise a status of the patch as covered or not covered.

In yet another embodiment of the present invention, there is provided single-use temperature measurement device for measuring core body temperature of a subject, comprising a flexible, folded substrate comprising a thermal zone on a top surface thereof; an electrically isolated annular copper ring disposed on the top surface of the flexible, folded substrate to surround the thermal zone; a first semi-circular copper component and a second semi-circular copper component both disposed on the top surface of the flexible, folded substrate inside the electrically isolated annular copper ring and both electrically isolated therewithin; a plurality of temperature sensors disposed within the thermal zone on the flexible, folded substrate and operably connected thereto; a top insulator disposed over the top surface of the flexible, folded substrate; a bottom flexible insulator formed with a central opening therethrough and disposed on a bottom surface of the flexible, folded substrate to cover sections thereon formed by the plurality of temperature sensors; a thermal plug disposed beneath the first semi-circular copper component and the second semi-circular copper component and within the central opening through the bottom flexible insulator; an adhesive disposed on the bottom surface of the flexible, folded substrate to removably secure to the subject; and means for connecting to a machine learning algorithm.

In this embodiment, the plurality of temperature sensors may comprise a first temperature sensor disposed in the thermal conducting zone between the first copper semi-circle and the second copper semi-circle; a second temperature sensor disposed on the flexible, folded substrate radially beyond the edge of the annular copper ring; a third temperature sensor disposed on the flexible, folded substrate between the annular copper ring and the copper circle or disposed on the annular copper ring; and a fourth temperature sensor disposed in a section of the flexible, folded substrate proximate to the first thermal sensor. Also in this embodiment, the thermal plug may be made from a low-density polyethylene. In addition, single-use temperature measurement device may be constructed for a single use of about 24 hours.

In yet another embodiment of the present invention, there is provided a system for measuring core body temperature in a subject, comprising the single-use temperature measurement device as described supra; and a machine learning algorithm tangibly stored on an electronic device having at least a memory and a processor, where the machine learning algorithm is configured to receive and analyze input data from the plurality of temperature sensors disposed on the temperature measurement device and from an environmental context sensor and to output at least the predicted core body temperature.

Provided herein is a low power, wearable, single use thermal device or temperature measurement device to accurately quantify core body temperature based on machine learning. The thermal device does not rely on a heater and is based on low-power thermal sensors or temperature sensors and supports wireless and low-power operation in resource-limited settings. The thermal device comprises multiple temperature sensors separated with insulating materials of different thermal conductivities to provide a well-defined thermal gradient to characterize the heat flux across the device. The machine learning algorithm accounts for heterogeneous, hard-to-measure parameters among subjects, such as tissue thermal conductivity and heat generation rate, and is trained to accurately quantify the core temperature in subjects with higher accuracy in core body temperature quantification compared to a multivariate regression model.

Generally, the thermal and temperature measurement devices are made of a flexible, foldable printed circuit board substrate, such as made of, but not limited to, a polyimide. The substrate is formed as a patch with insulating materials, electrical isolated copper, a plurality of thermal sensors or temperature sensors, and an adhesive to removably adhere or secure the device to the subject, such as a patient for a medical or surgical procedure. As is known in the art, the foldable substrate forming the patch comprises circuit traces and electrical pads to operably and electrically link the thermal sensors. The device is removably adherable to the subject's body, for example, but not limited to, the forehead.

The device is wirelessly linkable, for example, via Bluetooth, to an electronic device, such as a smart device, comprising at least one memory, a processor and at least one wireless network connection. The electronic device tangibly stores applicable algorithms, such as a machine learning algorithm, executable thereby. The device is configured for single or one-time use and transmits temperature data as input to the machine learning algorithm for a period of about 24 hours. The machine learning algorithm receives, as input, temperature data and, optionally, environmental context data, such as ambient data, for example, but not limited to, ambient or room temperature data and/or ambient air velocity, and/or whether or not the patch is covered, such as with a bandage or with a temperature management device that covers the subject's or patient's head, and/or patient data, for example, but not limited to, the sex of the subject, body mass index of the subject or time or length of a menstrual cycle or a combination thereof. The machine learning algorithm outputs the predicted core body temperature to the electronic device which displays and/or stores the same as is known in the art.

The thermal devices provided herein have a low-power design for mobile battery powered use cases and do not need to be tethered to wall power. The thermal devices provided herein are useful to monitor patients more easily before, during, and after surgery or other medical procedure. Moreover, the patients may be monitored in transit. Furthermore, the portability and less electrical power requirements are useful for military field surgery.

The following examples are given for the purpose of illustrating various embodiments of the invention and are not meant to limit the present invention in any fashion.

Example 1

Methods and Materials

Materials

Flexible PCB containing four temperature sensors (Maxim 30208) were manufactured and provided by Maxim Integrated. 3M™ SpotOn™ ZHF temperature monitoring system and patches were purchased from 3M. Jaybird & Mais Adhesive Foam and silicone adhesive were purchased from Amazon. Low-density polyethylene was purchased from US Plastic Corp. Double-sided adhesive (Avery MED 3044) was obtained from Avery Dennison.

Design and Fabrication of Wearable Thermal Devices

Figure 1B:
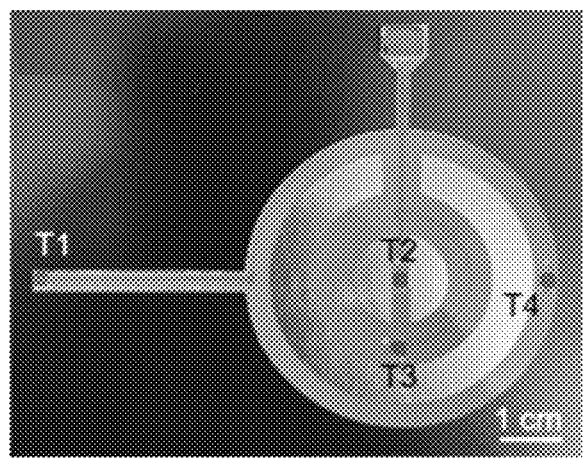
Figure 1C:
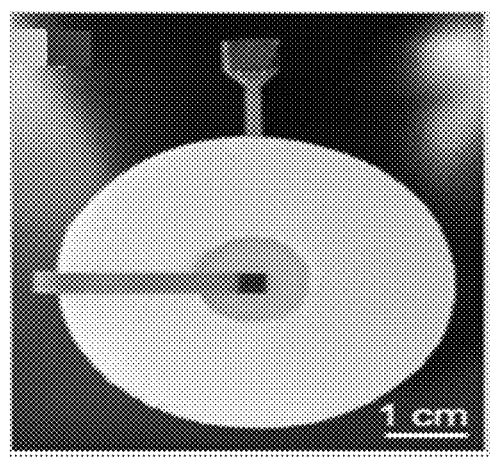
Figure 1D:
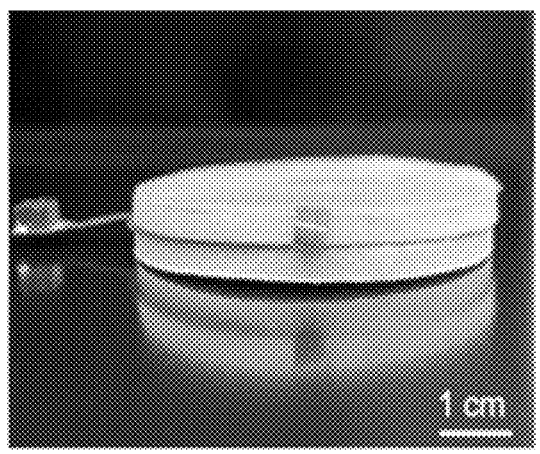

A soft wearable thermal device was designed to provide accurate quantification of core body temperature from the forehead or other locations on subjects, such as patients requiring such monitoring. Mechanically compliant wearable devices provide a seamless interface with the human skin, which is important for the accurate monitoring of physiological parameters (20-31). FIG. 1A highlights the main components of the thermal device. The device comprises four temperature sensors separated by the materials with different thermal conductivities to accurately quantify the core body temperature. These temperature sensors have been used in soft electronic devices for continuous body temperature monitoring (32-34). The temperature sensors provide 0.1° C. accuracy and 16-bit temperature resolution (0.005° C.) with a supply voltage range of 1.8 V. The temperature values were read every second in a one-shot method. The four sensors were placed on a flexible printed circuit board (PCB) made of polyimide with a thickness of 200 µm (FIG. 1B). A thin layer of copper pattern (17 µm) on the PCB facilitates homogeneous temperature distribution across the device. One temperature sensor is located in the center of the PCB, two sensors are located at the middle and edge, and the fourth sensor is located on the tip of a flexible ribbon, bent towards the center of the PCB (FIG. 1C). The temperatures measured by these four sensors are denoted as T1, T2, T3, and T4, respectively (FIG. 1B). The top surface of the PCB was encapsulated with a thermal insulating foam with a diameter of 50 mm and thickness of 3 mm. The insulating foam is made of styrene butadiene rubber with thermal conductivity of 0.05 W/m*K. Soft porous foams have been reported as a class of functional materials to provide conformal contact with the skin in skin-interfaced electronic devices (35-38). The Young's modulus of the soft foam used here was measured to be 1.6 kPa, much lower than the skin modulus of ~1 Mpa (39). A concentric insulating foam with a thermal plug in the center was sandwiched between the flexible ribbon and PCB (FIGS. 1B, 1D), resulting in a temperature gradient along the in-plane and out-of-plane directions of the device. The thermal plug has a diameter of 15 mm and is made of three layers of low-density polyethylene (LDPE) with thermal conductivity of 0.34 W/m*K. The top and bottom LDPE layers have a square opening to fit the temperature sensors on the PCB. A medical-grade double-side skin adhesive (Avery MED 3044) was used to robustly bond these different layers and form a robust interface between the wearable device and the skin. All those components can be fabricated with low-cost, high throughput approaches, including die cutting for the soft foam and adhesives of different geometries and waterjet cutting for the LDPE thermal plugs. It is important to eliminate air pockets when assembling various layers in device fabrication for consistent performance. FIG. 1D shows an optical image of a fully assembled thermal device with a partially exposed flexible ribbon and flat skin-facing surface.

Material and Device Characterization

A hot disc thermal conductivity analyzer (TPS 2500) was used to measure the thermal conductivity, thermal diffusivity, and specific heat of materials, including insulating foam and LDPE. A heating power of 2.5 mW and a measurement time of ten seconds were used in the thermal characterization. The thermal conductivity and thermal diffusivity of the insulating foam were measured to be 0.05 W $m^{-1}K^{-1}$ and 0.36 $mm^2$ $s^{-1}$. The thermal conductivity and thermal diffusivity of the LDPE were measured to be 0.34 W $m^{-1}K^{-1}$ and 0.22 $mm^2$ $s^{-1}$.

Figure 3A:
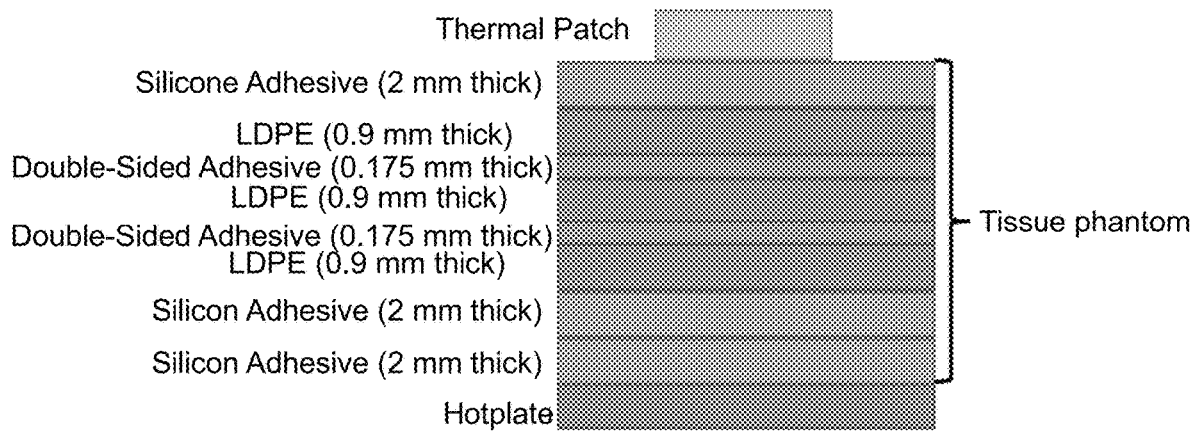
FIGS. 3A-3F illustrate device testing with a tissue phantom.

The thermal devices were first tested on a tissue phantom before in vivo measurements (see FIG. 3A). A separate temperature sensor was placed directly on the hot plate surface beneath the tissue phantom to simulate core body temperature. The thermal devices were placed on the phantom with the center aligned with the temperature sensor beneath the phantom. The hotplate was adjusted to different temperatures, from 35.5° C. to 40° C., covering physiologically relevant CBT. The temperature sensors on the hotplate surface were continuously recorded with an Omega Quadrtdtemp Logger. The four temperatures inside the thermal devices were recorded using MAX30208 thermometers with the MAX30208 EVKit Tool software. The temperature sensors (MAX30208) converted the temperature measurements to digital form using a high resolution, sigma-delta, analog-to-digital converter (ADC). A combination of MAX30208EVSYS interface board with MAX32630 microcontroller feather board was used and connected to the PC via a USB line. The communication is through an inter-integrated circuit (I2C), and 2-wire serial interface. The I2C (SDA, SCL, VDD, GND) lines were stemmed from the MAX30208EVSYS evaluation board and were fed to the flexible circuit inside the devices where the four temperature sensors were located at four different locations. All the temperatures were simultaneously and continuously collected until temperatures reached a steady state. A steady state was defined when temperature changes were less than 0.2° C. over five minutes. Human subjects, including 6 females and 6 males, were recruited for in vivo tests. The potential risks of the study were explained to recruited human subjects, and informed consent, including publication of human subject photographs, was obtained after the procedure. One thermal device and one ZHF device were placed on the forehead of human subjects. The temperature data were simultaneously recorded for around 15 minutes until the temperature reached a steady state. Infrared thermal images of devices on the forehead were collected with a thermal imager (FLIR E54). All tests involving human subjects were performed under approval from the Institutional Review Board at Texas A&M University.

Thermal Power Calculations

The four temperature sensors were used to quantify the power transfer across the device with equations E1-E4. Three thermal paths are assigned through the thermal plug, through the insulating material under the temperature homogenizing copper layer and through the insulating material at the edge of the device.

$$\text{Power Transfer}_{plug} = \tag{E1}$$

$$(T_1 - T_2) \times \frac{\text{Thermal Conductivity}_{plug}\left[\frac{W}{m \cdot K}\right] \times \text{Area}_{plug}[m^2]}{\text{Plug Thickness}[m]}$$

$$\text{Power Transfer}_{insulator\text{-}copper} = \tag{E2}$$

$$(T_1 - T_3) \times \frac{\text{Thermal Conductivity}_{insulator\_copper}\left[\frac{W}{m \cdot K}\right] \times \text{Area}_{insulator\_copper}[m^2]}{\text{Plug Thickness}[m]}$$

$$\text{Power Transfer}_{insulator\text{-}edge} = \tag{E3}$$

$$(T_1 - T_4) \times \frac{\text{Thermal Conductivity}_{insulator\_edge}\left[\frac{W}{m \cdot K}\right] \times \text{Area}_{insulator\_edge}[m^2]}{\text{Plug Thickness}[m]}$$

$$\text{Power Transfer}_{device} = \text{Power Transfer}_{plug} + \tag{E4}$$
$$\text{Power Transfer}_{insulator\text{-}copper} + \text{Power Transfer}_{insulator\text{-}edge}$$

$$\text{Power Transfer}_{phantom} = \tag{E5}$$

$$(T_{core} - T_1) \times \text{Thermal conductance}_{tissue\ phantom}\left[\frac{W}{K}\right]$$

$$T_{core} = T_1 + \frac{\text{Power Transfer}_{patch}}{\text{Thermal conductance}_{Phantom\ tissue} \times R} \tag{E6}$$

The constant R=~0.8 is associated with the thermal resistance between the tissue phantom and the device and the loss thereon. The core body temperature is approximated to a linear combination of the four temperature readouts. The relationship forms the basis to quantify CBT using a multivariate linear regression model.

Example 2

Simulations and Phantom Testing
Thermal Simulation of Devices

Figure 2A:
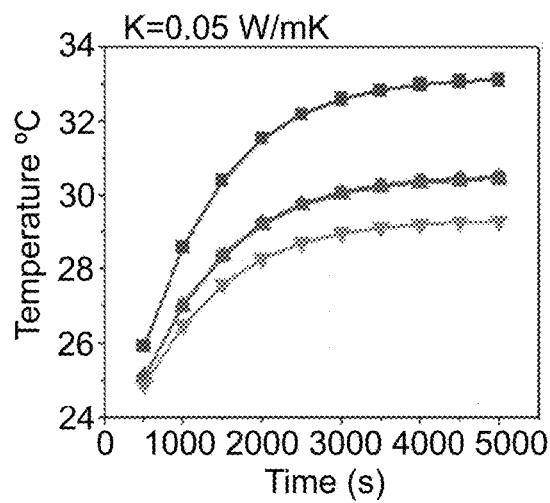
FIGS. 2A-2G show thermal simulations of the device.
Figure 2B:
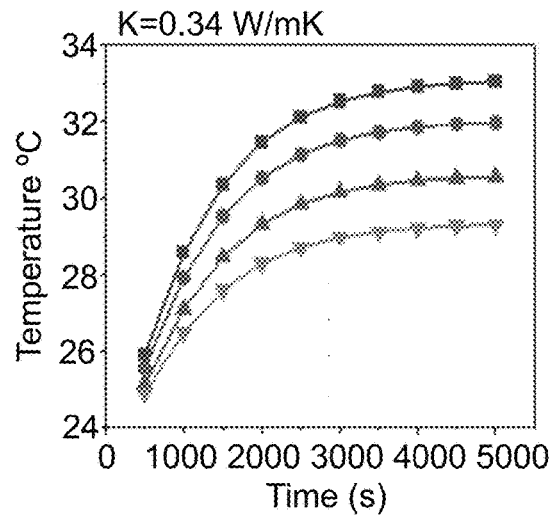
Figure 2C:
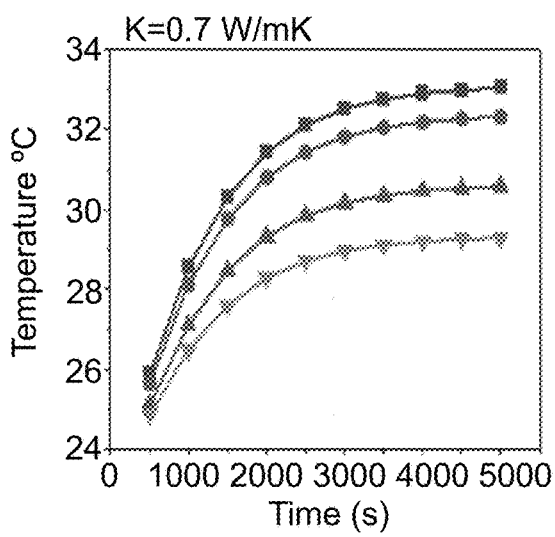
Figure 2D:
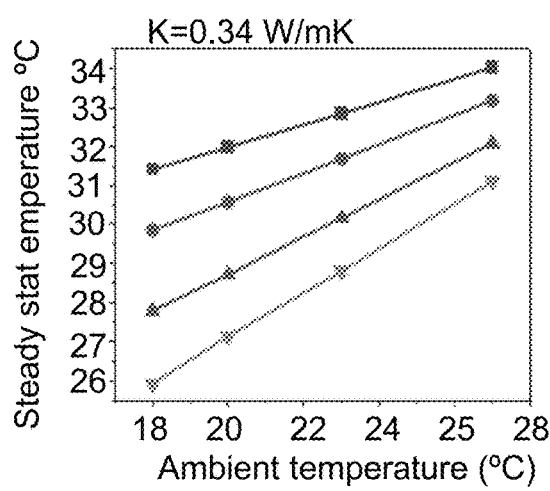
Figure 2E:
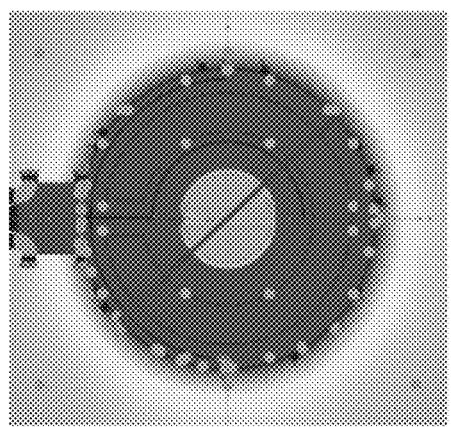
Figure 2F:
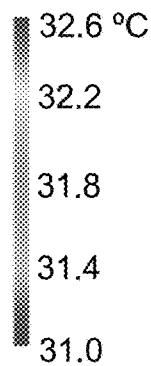
Figure 2F:
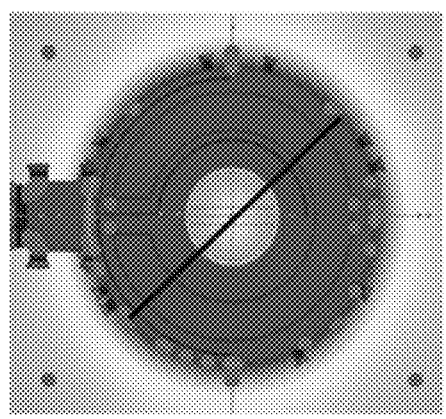
Figure 2G:
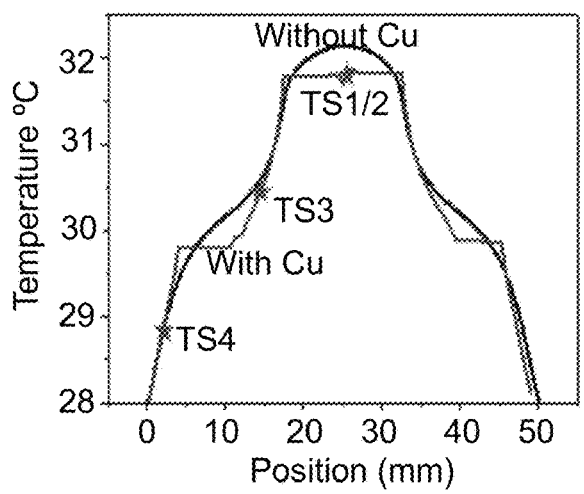

A thermal simulation was performed with SolidWorks finite element analysis to optimize the design parameter of the thermal device. In the simulation, the core temperature was set to 37° C., and the heat transfer convection coefficient for air is 5 W m$^{-2}$K$^{-1}$ with an ambient temperature of 23° C. Thermal radiations towards the ambient environment were set via defining specific emissivity values for all outer surfaces of the patch and the simulated tissue. The emissivities of the skin, the top surface of the device, and the insulating foam were set to 0.98, 0.68, and 0.6, respectively (40). The thermal conductivity of the thermal plug was optimized to maximize the temperature difference quantified by the four sensors. FIGS. 2A-2C show the temperature changes at the sensor location over time with varying the thermal conductivity of the thermal plug from 0.05 to 0.7 W/mK. The overall temperature T1 below the thermal plug is higher than temperature T2 above the plug, following the temperature decrease from the core temperature to the ambient in the out-of-plane direction. The lateral temperature decreases radially from center T2 to middle T3 to edge T4, following the decreased lateral thermal conductivity from the thermal plug to the insulating foam. In all cases, the temperature difference between T1 and T4 is around 3.8° C. at the steady state. With the thermal conductivity of 0.05 W/mK, the steady state T2 and T3 follow the same FIG. 2A). With the thermal conductivity of 0.7 W/mK, the steady state temperature difference between T1 and T2 is 0.7° C. (FIG. 2C). With the thermal conductivity of 0.34 W/mK, the steady state temperature difference between the four sensors falls in the range of 1.0-1.4° C. (FIG. 2B). These results show that an LDPE thermal plug with thermal conductivity of 0.34 W/mK enables maximum thermal gradient in three dimensions and provide equal temperature differences at the location of four thermal sensors. A thermal simulation was performed with varying ambient temperatures and further validated this trend to be consistent (FIG. 2D). Such design can minimize the CBT uncertainty resulted from the limited accuracy of off-the-shelf thermometers (0.1° C.). Therefore, LDPE thermal plugs are used in the devices for the following simulation and tests. FIGS. 2E-2F show the top-view temperature distribution of the encapsulated device with and without the Cu pattern. The temperature decreases radially from the center to the edge of the device following the decreased thermal conductivity from LDPE to insulating foam (FIG. 2G). The device with the Cu pattern shows a uniform temperature distribution in the Cu region and a linear thermal gradient in the rest regions. In contrast, the device without the Cu pattern exhibits a nonlinear thermal gradient. The four temperature sensors are highlighted in the profile to visualize their lateral locations. The addition of the copper plane in the flex PCB keeps a constant thermal gradient across the regions of the PCB over the thermal plug and insulating foam. This is particularly important to reliably quantify the power transfer across the device including the plug and insulating foam regions (Eq. 1-Eq. 4). A temperature homogenizing copper layer ensures that a single temperature readout can represent the average temperature of the region where the thermometer is located. The core body temperature can be approximated to a linear combination of the four temperature readouts (Eq. 5-Eq. 6). This relationship forms the basis to quantify CBT using a multivariate linear regression model in vitro and in vivo discussed below. This design ensures radially uniform, vertical flows of heat across the thermal plug and insulating foam can be well characterized by four temperature readouts.

Device Testing with Tissue Phantom

A tissue phantom was used to characterize and validate the consistent performance of thermal devices before using them on human subjects. The devices with inconsistent performance due to fabrication error were below 10% and not used in human subject studies. It is important to note that calibrating individual devices with tissue phantom is not needed for their in vivo applications with the optimized fabrication. The forehead is composed of the epidermis, dermis, cortical bone, fat, facia, and retaining ligaments with different thermal properties. The thermal conductivity of these components was collected from literature to determine the materials needed to construct the tissue phantom (Table 1) (9, 41).

TABLE 1

Thermal Conductivity and Thickness of Components of the Forehead

| Forehead components | Thermal Conductivity (W/m * K) | Thickness (mm) |
| --- | --- | --- |
| Cortical Bone | 0.32 | 10.00 |
| Facia | 0.39 | 0.15 |
| Retaining Ligament | 0.47 | 0.50 |
| Subcutaneous Fat (SAT) | 0.21 | 2.50 |
| Fat | 0.21 | 1.61 |

TABLE 1-continued

Thermal Conductivity and Thickness of Components of the Forehead

| Forehead components | Thermal Conductivity (W/m * K) | Thickness (mm) |
|---|---|---|
| Dermis | 0.76 | 2.24 |
| Epidermis | 0.13 | 0.15 |

Figure 3B:
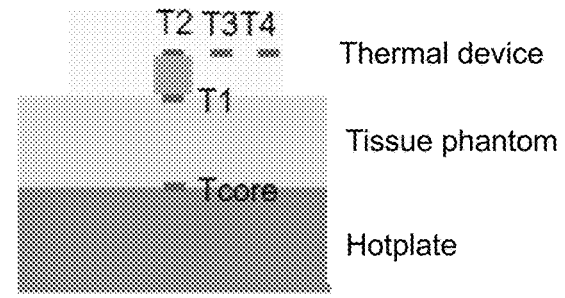
Figure 3C:
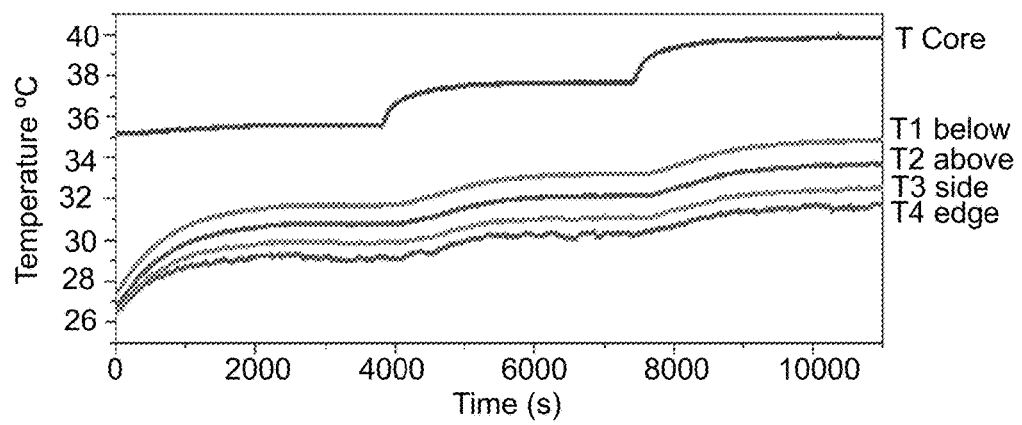

The tissue phantom was constructed with three layers of LDPE, two layers of the double-sided adhesive, and three layers of silicone adhesive to achieve the similar thermal conductance as the forehead (FIG. 3A). The thermal devices were placed on the tissue phantom laminated on the hotplate, which provides the simulated core temperature (FIG. 3B). The hotplate temperature was set to various temperatures from 35° C. to 40° C., simulating normal and abnormal core body temperature. A thermal sensor beneath the tissue phantom aligned to the center of the thermal device continuously records the simulated CBT (Tcore). Simultaneously, the four temperature sensors inside thermal devices record the corresponding temperatures every 5 seconds (FIG. 3C). All the temperature T1-T4 increases with the increase in the Tcore and reaches a steady state right after Tcore. The temperature decreases from the core to the ambient across the tissue phantom and thermal device and decreases from the center to the edge of the device. The three-dimensional thermal gradient is consistent with the simulated results above. The temperature difference at the four sensor locations increases with the increase in Tcore. The steady state T1 is 2.5° ° C., 2.9° C. and 3.3° C. higher than T4 with the Tcore of 35.5° C., 37.7° C. and 39.8° C., respectively.

Figure 3D:
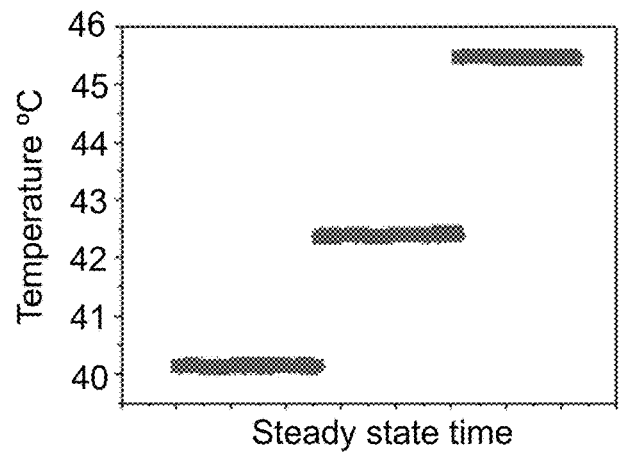
Figure 3E:
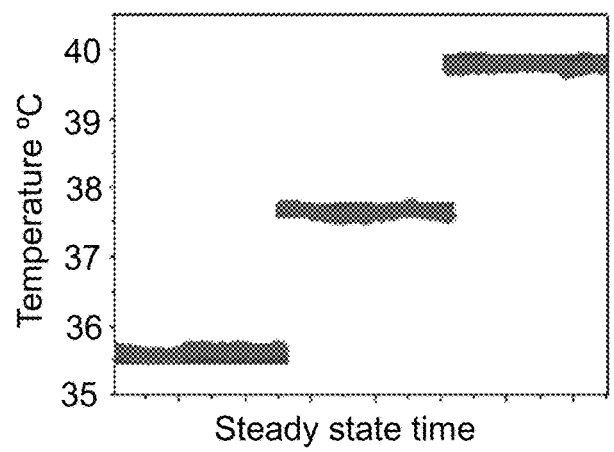
Figure 3F:
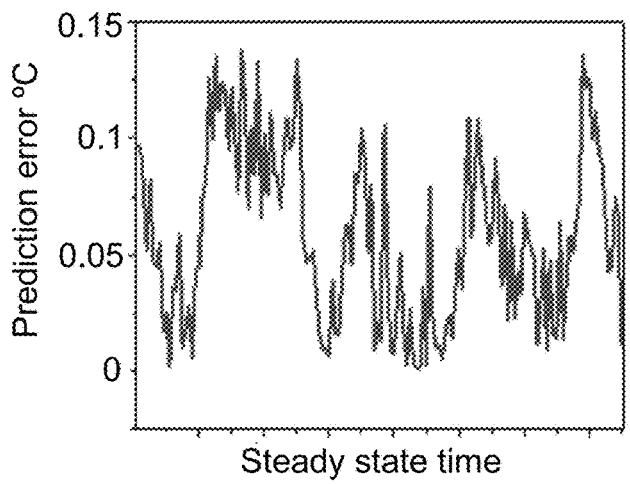
Figure 4A:
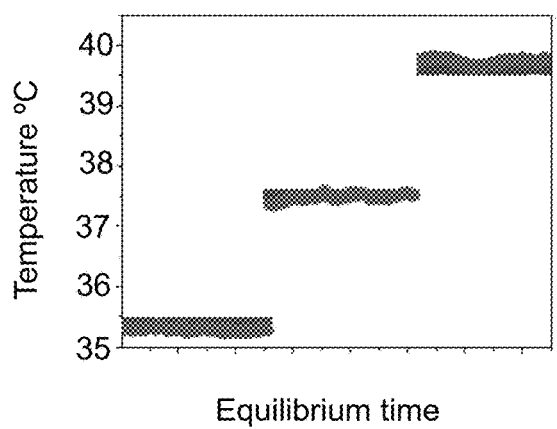
FIGS. 4A-4D show Tcore predictions with another two thermal devices (FIGS. 4A, 4C) and the corresponding prediction errors (FIGS. 4B, 4D).
Figure 4B:
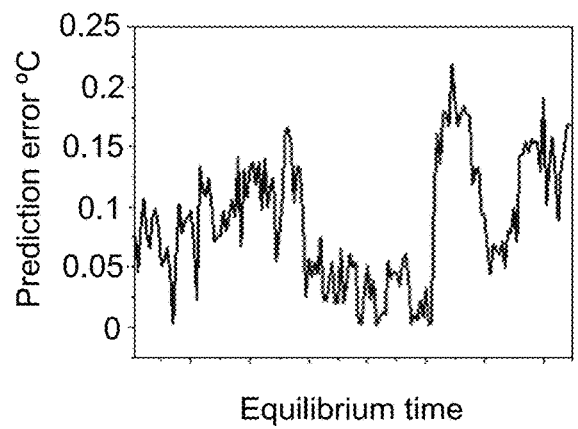
Figure 4C:
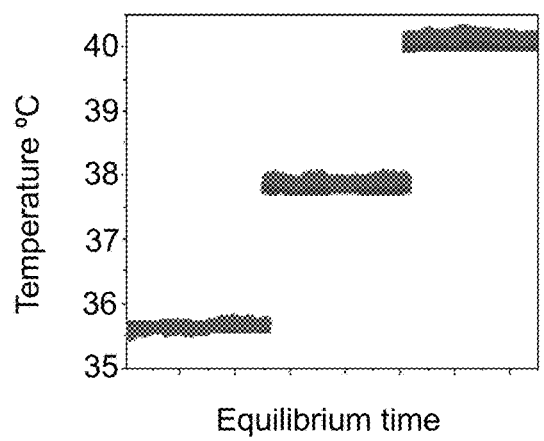
Figure 4D:
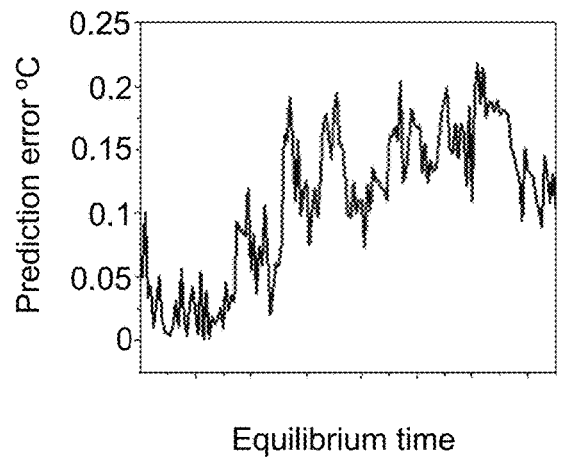
Figure 8A:
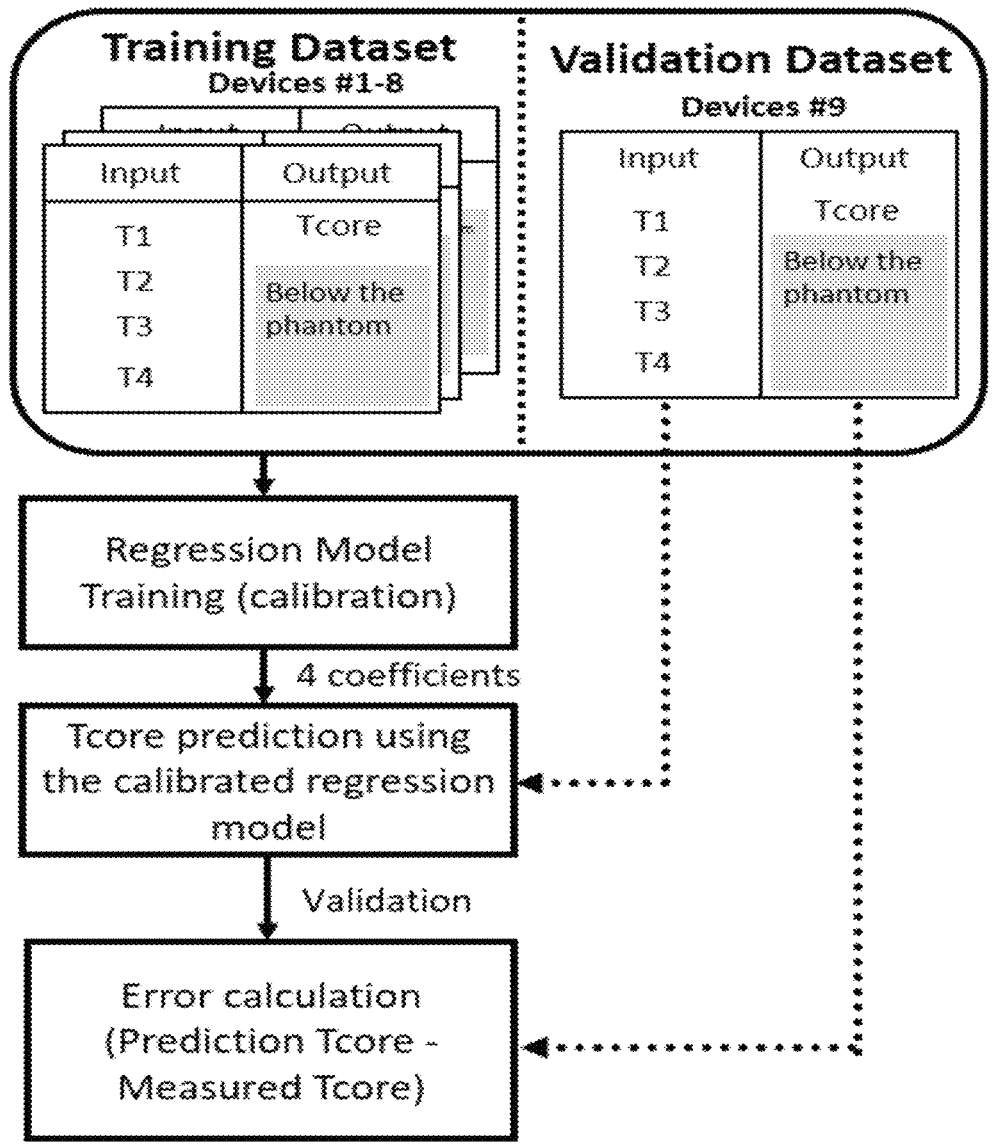
FIGS. 8A-8C are model calibrations and validations. Flow diagrams of calibration and validation of the multivariate linear regression model are shown in tests using tissue phantom (FIG. 8A) and in vivo (FIG. 8B).

A multivariate regression model was used to quantify core body temperature. The temperature sensor below the tissue phantom and the four internal temperature sensors produce temperature readings every 5 seconds. The readings from the sensor below the phantom (Tcore) were used as the output, and the four internal temperatures (T1-T4) were the input data to train a multivariate regression model and calculate its coefficients. At each emulated steady state core body temperature, 50 data points spanning over 250 see were simultaneously collected from the above-mentioned temperature sensors. Nine thermal devices were examined by the CBT sweep protocol using a hotplate as a heat source while the hotplate surface temperature simulates normal and abnormal core body temperature. The data collected from 9 devices were used from calibration and validation of the multivariate regression model (see FIG. 8A). First, the data from devices #1-8 were used to train and calibrate the multivariate regression model, which yields to a linear combination of the four temperatures and coefficients using MATLAB. Subsequently, the calibrated model was used to predict Tcore using the data collected from device #9 and compare it with the measured Tcore in the validation phase. FIG. 3D shows the measured and estimated core body temperature temperatures with the four temperatures collected from 8 devices fed to the regression model for calibration. For validation, the Tcore predicted by the calibrated model is consistent with the measured Tcore (FIGS. 3E, 4A, 4C). The prediction error is less than 0.25° C., well below 0.5° C. (FIGS. 3F, 4B, 4D).

Example 3

Testing In Vivo
Device Testing on Human Subjects

Figure 5E:
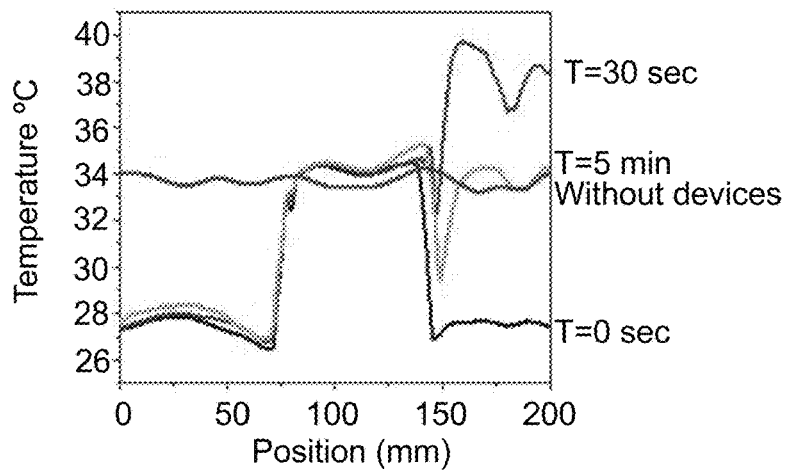

After confirming the consistent performance of the thermal devices in the tests involving tissue phantom, they were tested on the foreheads of healthy human subjects. Previous work showed that the ZHF devices placed on both sides of the forehead exhibit a negligible difference in the quantified Tcore (12). Therefore, the ZHF and the thermal devices were placed symmetrically on both sides of the forehead for testing. The ZHF device measured CBT serves as a reference for the calibration and validation of our devices. The thermal device is laminated onto the foreheads of the subjects for conformal contact of the soft, flexible device on the skin. A thermal imager was used to visualize and to quantify the skin temperature changes before and after applying these two devices. Without the presence of the devices, the forehead temperature is about 34° C., falling within the normal range of forehead temperatures from 31.0° C. to 35.6° C. reported in the literature (FIGS. 5A, 5E) (42). After both devices were applied to the forehead, the skin temperature showed negligible changes (FIGS. 5B, 5E). The device's outer surface temperatures are 6° C. lower than the skin temperature. After the ZHF device was initiated, the heater inside immediately raised temperature, evidenced by the 10° C. increase in the device surface temperature after the device activation (FIGS. 5C, 5E). The ZHF surface temperature stabilized to be similar to the skin temperature after 5 minutes (FIG. 5D). FIG. 5E shows the quantitative comparison of the temperature changes under those conditions described above. It is worth noting ZHF device increased the local skin temperature surrounding the device by ~1° C. because the active heating equilibrates the temperature from the underlying tissue to the skin. In contrast, the presence and operation of our thermal devices do not deliver the heat to the forehead thereby altering the skin temperature.

Figure 5F:
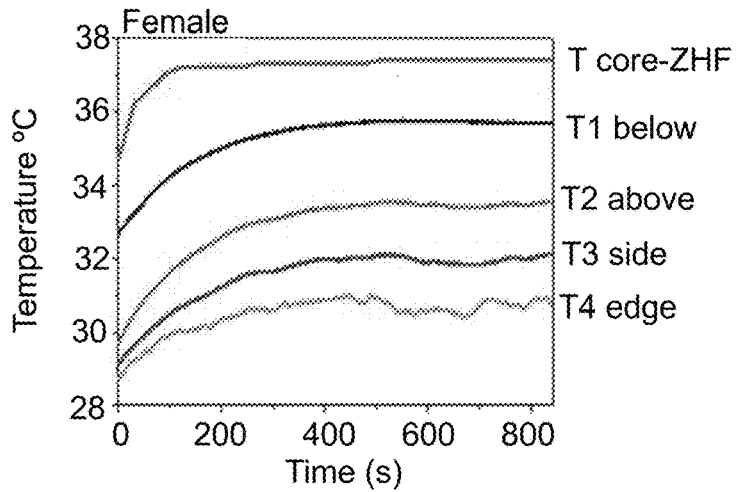
Figure 5G:
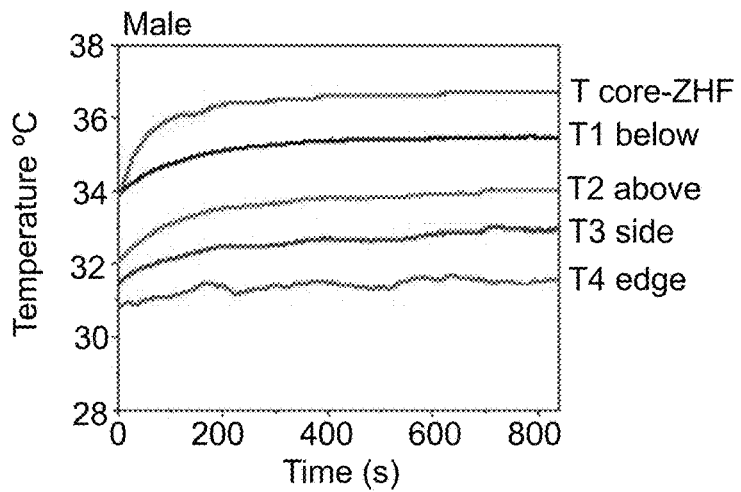

The temperatures with the ZHF and the thermal devices were continuously and simultaneously recorded immediately right after the devices were applied to the forehead of 6 female and 6 male human subjects. FIG. 5F shows the Tcore measured with the ZHF device and T1-T4 measured with our device on a female forehead. The temperature measured by the ZHF device reaches a steady state temperature of 37.2° C. in 3 minutes, while the temperature measured by our device reaches a steady state in 6 minutes. The steady-state T1 on the skin surface is 35.7° C., lower than the T core by 1.5° C. The temperature decreases from the Tcore to T1 to T4 across the patch, both in-plane and out-of-plane. The steady-state T1 is 5° C. higher than T4 and this temperature difference is larger than 2.9° C. obtained in the tests using tissue phantom. FIG. 5G shows a representative temperature profile collected from a male forehead. The temperature measured by the ZHF device reaches a steady state temperature of 36.4° C. in 3.5 minutes, while the temperature measured by our device reaches a steady state in 6 minutes. It takes shorter time to reach steady state in vivo than that in the measurements using tissue phantom shown in FIGS. 3A-3F. The difference primarily results from different thermal properties and thicknesses between living tissue and phantom and the absence of heat generation in the phantom. Alternatively, an exponential model can be potentially utilized to estimate the equilibrium temperature before reaching the steady state to further shorten the acquisition time, which will be explored in a separate study. The steady-state T1 on the skin surface is 35.3° C., low than that of Tcore by 1.1° C. The steady-state T1 is 4° C. higher than T4, lower than that in female measurements. On average, it was observed that female subjects have higher CBT than males, consistent with the previous report (43).

Quantification of Tcore Based on Regression Models and Machine Learning

Figure 6A:
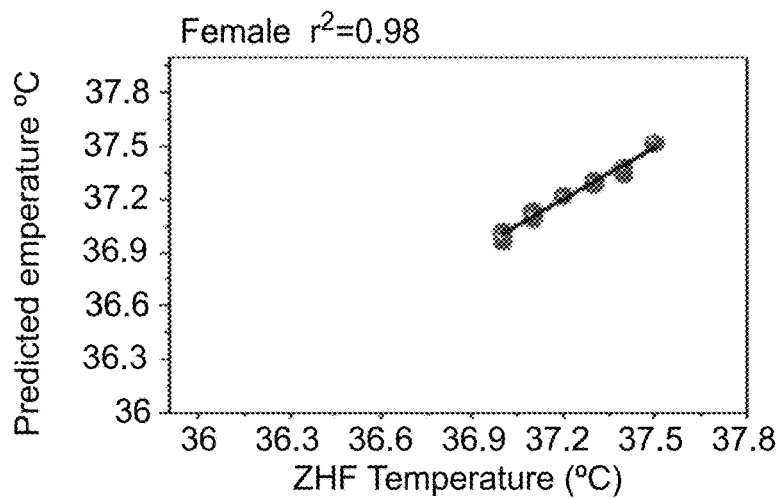
FIGS. 6A-6F are core temperature quantifications based on regression models. Tcore quantifications are shown using temperatures collected on female subjects (FIG. 6A), male subjects (FIG. 6B), and combined female and male subjects (FIG. 6C), and the corresponding errors (FIGS. 6D-6F), respectively.
Figure 6B:
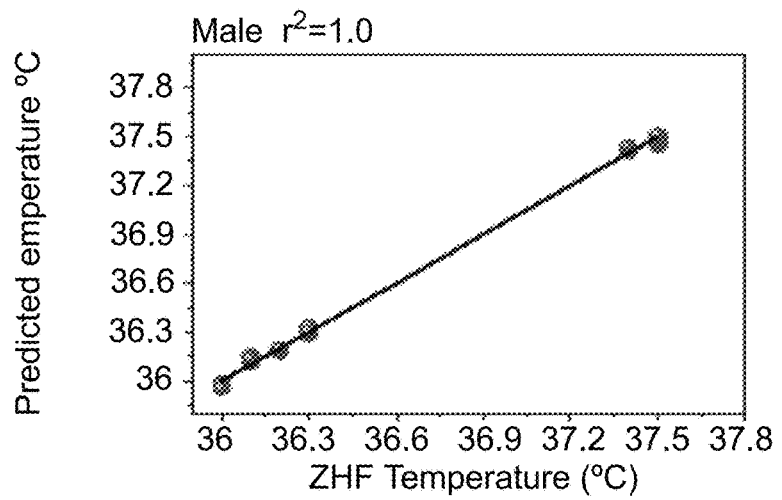
Figure 6C:
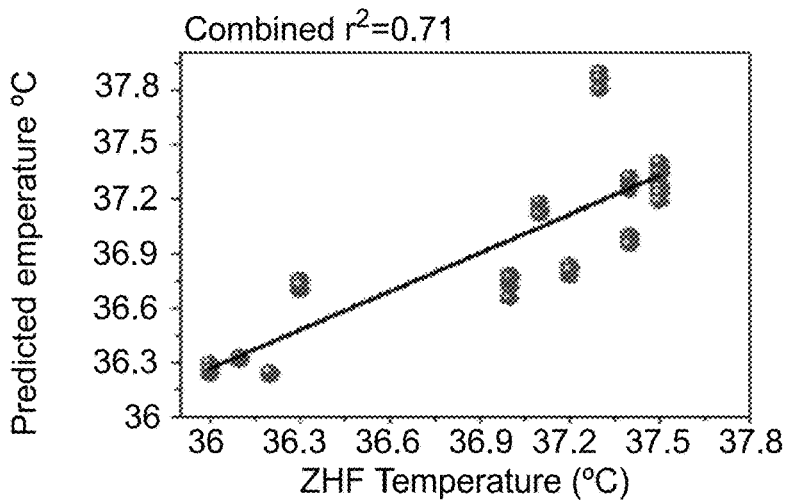
Figure 6D:
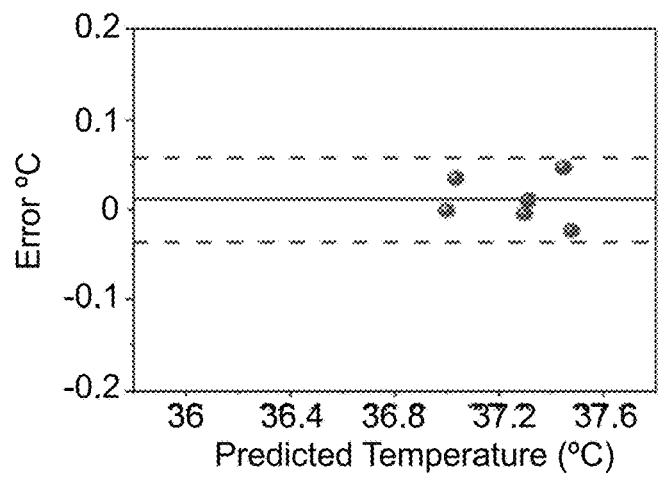
Figure 6E:
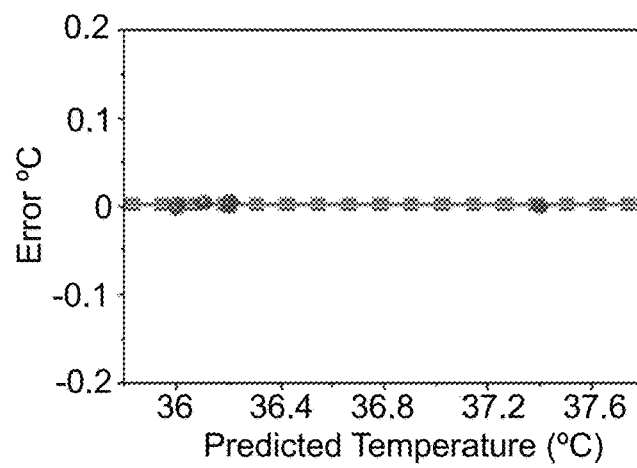
Figure 6F:
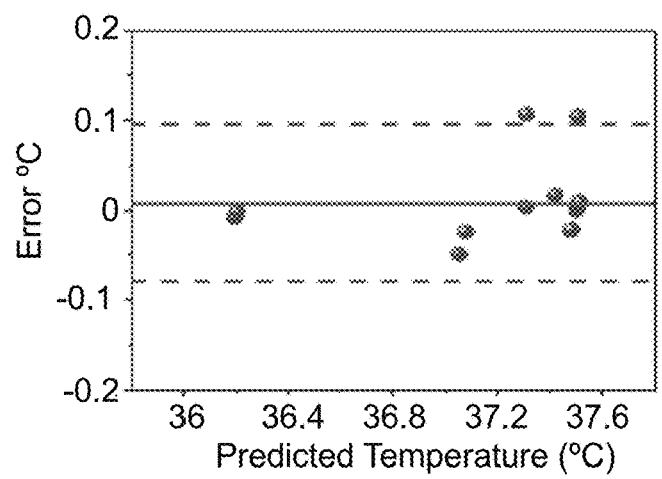
Figure 8B:
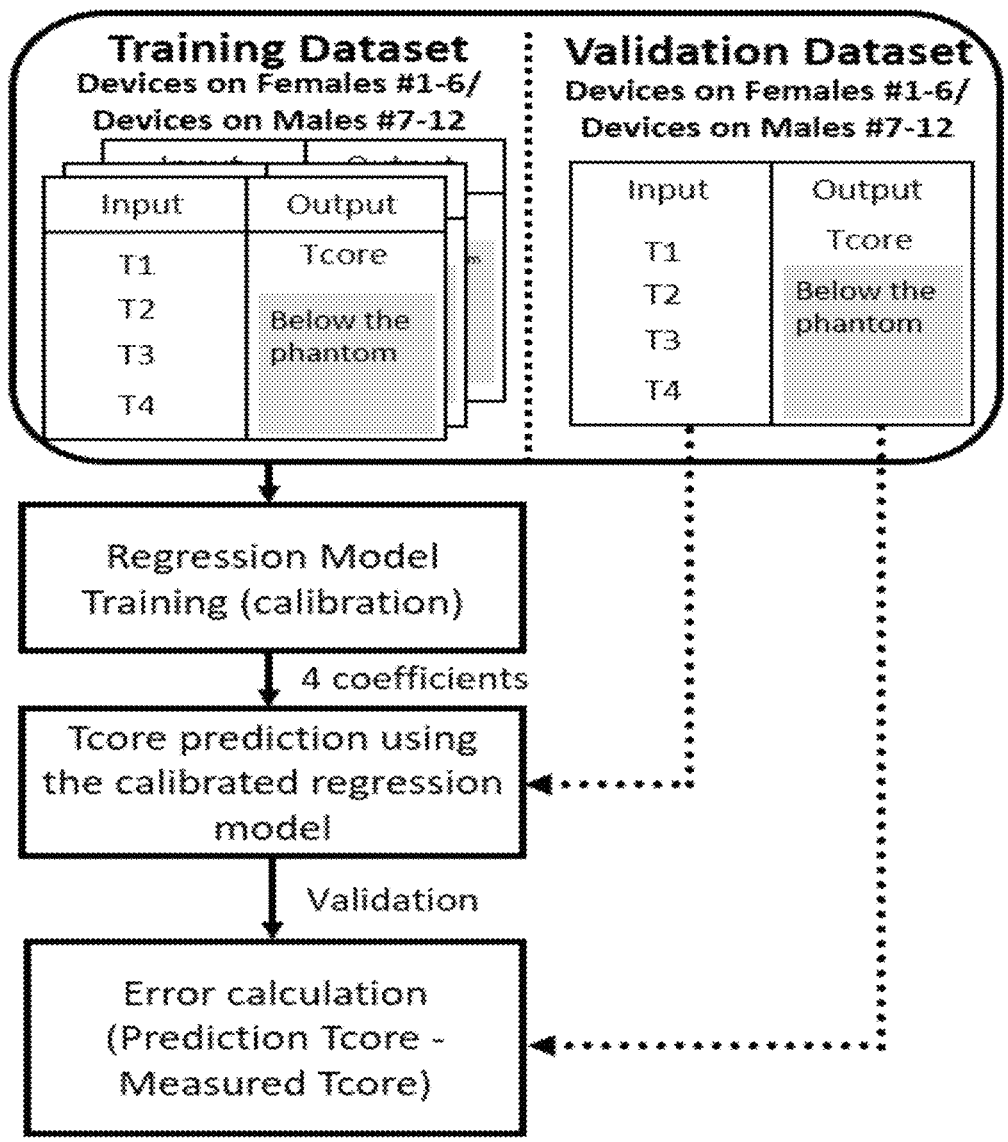

For in vivo experiments, data collected with 6 of the thermal devices and 6 of ZHF devices placed on female subjects and the same number of devices placed on male subjects was used to calibrate and validate the multivariate linear regression model. To maximize the training power, the data from all the devices were used to train and calibrate the regression model and then the calibrated model was used to predict each of these devices and compare the predicted Tcore with the measured Tcore (FIG. 8B). Each temperature sensor provides 6 data points with 30-second intervals in a steady state duration of 3 minutes per trial. The human trials were conducted on 6 male and 6 female subjects creating 36 data points per sex. Using MATLAB, three multivariate linear regression models were trained with three datasets containing the male, the female, and the combined male and female data points, respectively. In each case, the obtained regression coefficients were used to quantify the CBT using the four temperatures recorded via our thermal devices. The correlation plot quantifies the R-squared correlation coefficient between the ZHF and our device-measured CBT to be 0.98, 1.0, and 0.71 for female, male, and combined subjects, respectively (FIGS. 6A-6C). The Bland-Altman plots show the agreement between the ZHF and our device-quantified CBT (FIGS. 6D-6F). The mean absolute error (MAE) of CBT was calculated to be 0±0.05° C., 0±0.06° C., and 0±0.6° C., for female, male, and combined subjects, respectively. The higher error for combined subjects can be attributed to different anatomical structures and physiology between females and males. Although the mean CBT shows excellent agreement for all cases, the limit of agreement with 95% confidence intervals for combined subjects exceeds 0.5° C. This indicates a linear model cannot accurately quantify the CBT and needs further improvement.

Figure 7A:
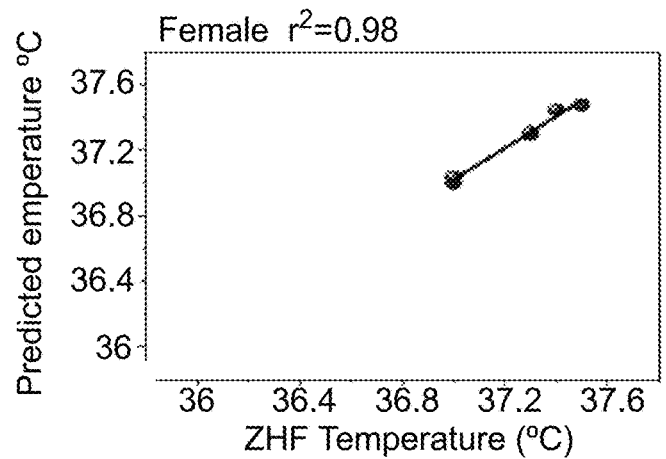
FIGS. 7A-7F are core temperature quantifications based on machine learning. Tcore quantification are shown using temperatures collected on female subjects (FIG. 7A), male subjects (FIG. 7B), and combined female and male subjects (FIG. 7C), and the corresponding errors (FIGS. 7D-7F), respectively.
Figure 7B:
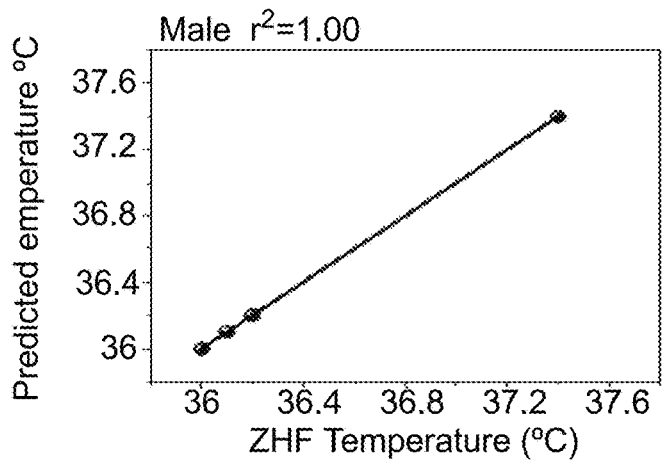
Figure 7C:
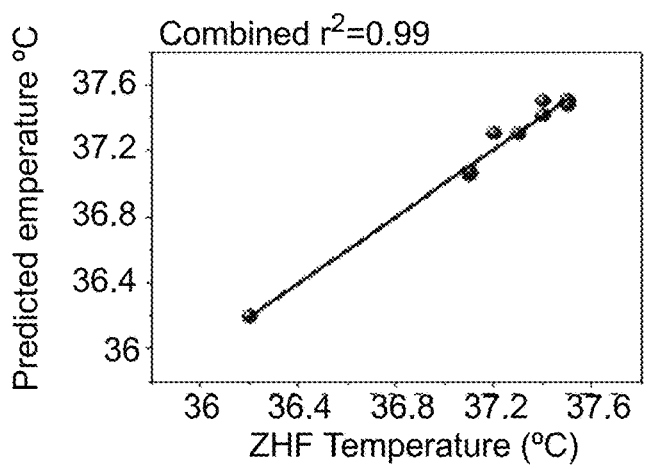
Figure 7D:
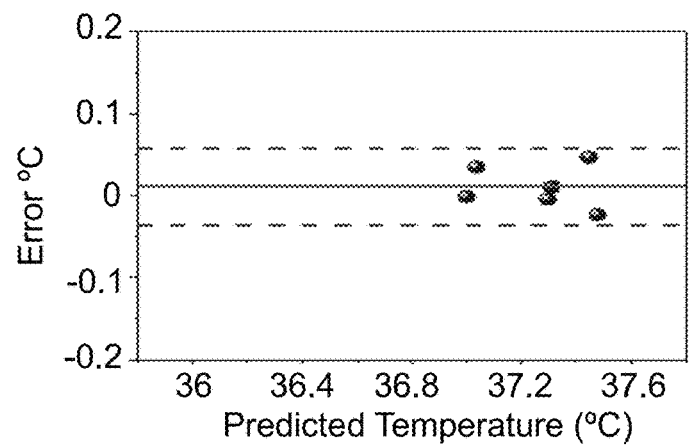
Figure 7E:
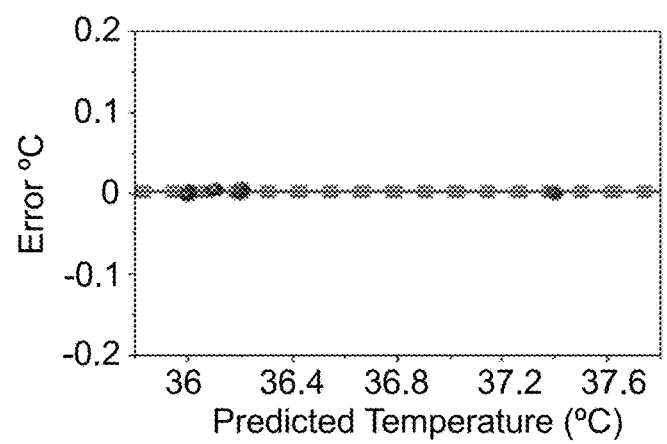
Figure 7F:
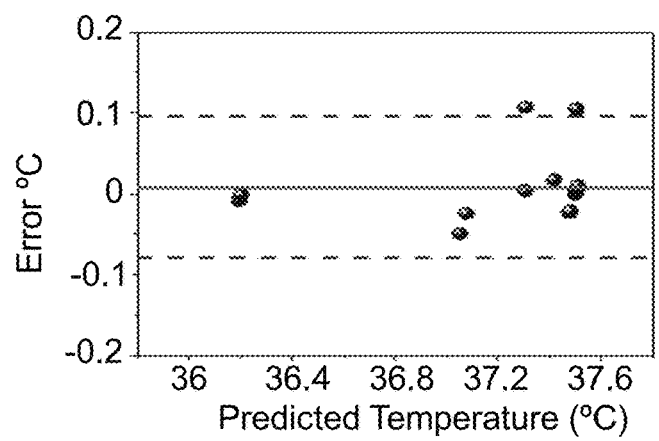
Figure 8C:
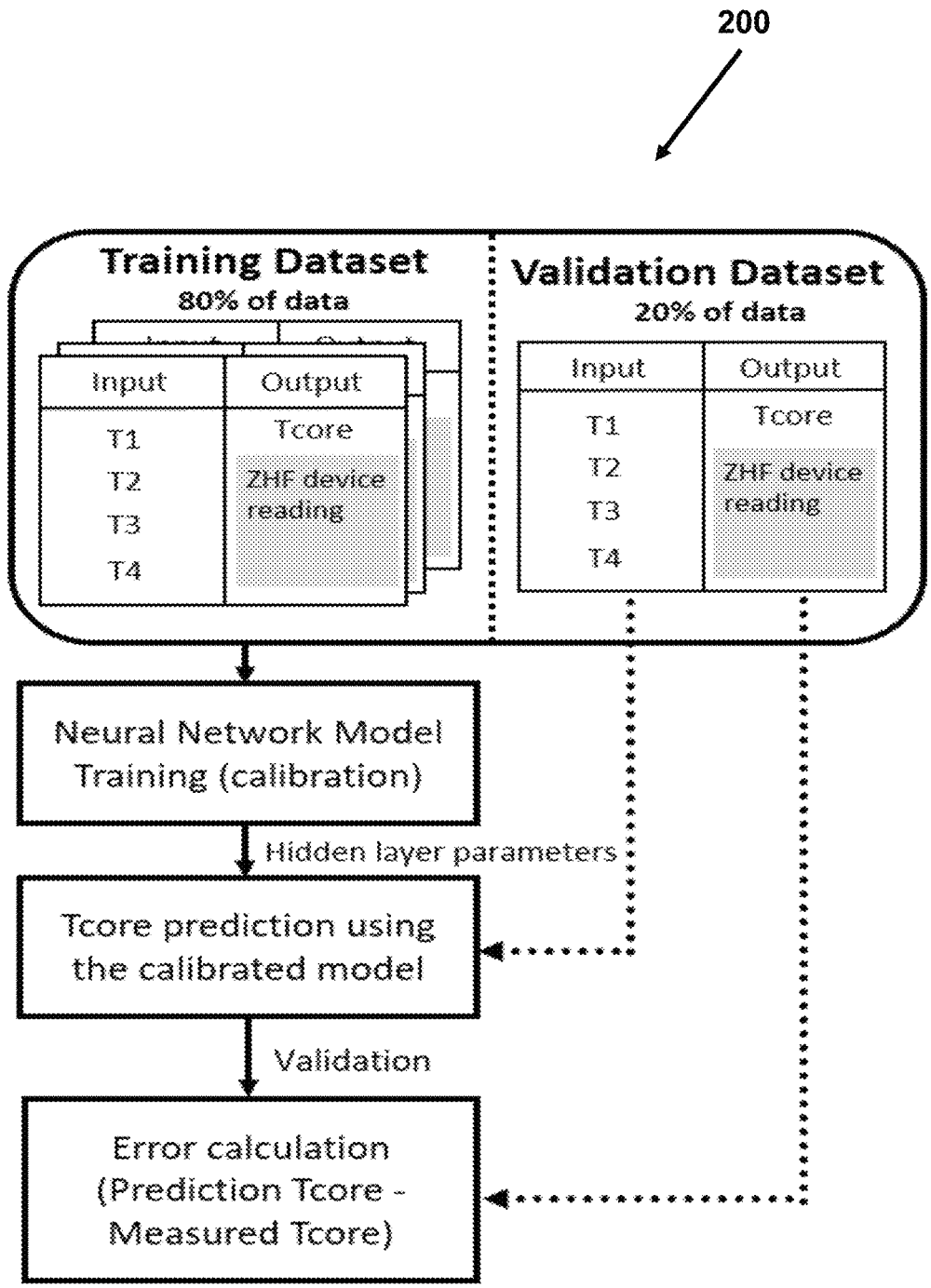

Next, a nonlinear machine-learning algorithm was employed to improve the accuracy of core body temperature quantification to mitigate the shortcomings of multivariate linear regression. The machine learning algorithm introduces a novel technique to account for heterogeneous, hard-to-measure parameters among individuals. These parameters include tissue thickness, thermal conductivity and heat generation rate. Parameters such as patient sex, body mass index, and menstrual cycle phase could be the input to the neural network-based machine learning algorithm. The four temperature readings (T1-T4) were used as input features, and the CBT temperatures measured by the ZHF devices were used as reference values. MATLAB was used to design and train the calibrating neural network that relates the four input temperatures to the CBT measured by the ZHF devices. The neural network has four input nodes followed by a hidden layer with a width of 50 nodes. The hidden layer is followed by a nonlinear "ReLu" activation layer and one output layer. This machine learning configuration can be implemented with a single microcontroller, which simplifies the integration of wearable sensors and miniaturized circuits. The machine learning algorithm was trained with three datasets containing the male, female, and combined male and female data for ten thousand iterations. In this case, 80% of all the data were used to train and calibrate the machine learning algorithm, and then the calibrated algorithm was used to predict Tcore and compare to the measured Tcore using the other 20% data in the validation phase (FIG. 8C). The correlation plot quantifies the R-squared correlation coefficient between the ZHF and the device-predicted core body temperature to be 0.98, 1.0, and 0.99 for female, male, and combined subjects, respectively (FIGS. 7A-7C). The Bland-Altman plots show the agreement between the ZHF and our device-quantified CBT (FIGS. 7D-7F). The CBT MAE was improved to 0.01±0.09° C. for combined subjects.

REFERENCES

1. A. Kurz, Best Practice & Research Clinical Anaesthesiology, 2008, 22:627.
2. Lim et al. Annals of the Academy of Medicine, Singapore 2008, 37:347.
3. Daniel et al. Anesthesiology, 2008, 109:318.
4. M. Faulds, T. Meekings, Continuing Education in Anaesthesia Critical Care & Pain, 2013, 13:75.
5. H. B. Simon, New England Journal of Medicine, 1993, 329:483.
6. Conway et al. Journal of Clinical Monitoring and Computing, 2021, 35:39.
7. Matsukawa et al. Anesthesiology, 1995, 82:1169.
8. Hymczak et al. International Journal of Environmental Research and Public Health, 2021, 18.
9. Wang et al. Anesthesia & Analgesia, 2016, 122.
10. Lefrant et al. Intensive Care Medicine, 2003, 29:414.
11. Lawson et al. Am J Crit Care, 2007, 16:485.
12. Lauronen et al. Journal of Clinical Monitoring and Computing, 2022, 36:1547.
13. Bräuer et al. Scientific Reports, 2020, 10:21746.
14. Erdost et al. J Anaesthesiol Reanim, 2021, 49:100.
15. Soehle et al. Journal of Clinical Monitoring and Computing, 2020, 34:1361.
16. Sessler et al. Anesthesiology, 1991, 75:985.
17. Mackowiak et al. Jama, 1992, 268:1578.
18. Feng et al. Physiological Measurement, 2017, 38:652.
19. Zhang et al. Advanced Healthcare Materials, 2016, 5:119.
20. Heikenfeld et al. Lab Chip, 2018, 18:217.
21. Ray et al. Chemical Reviews, 2019, 119:5461.
22. Tian et al. Nature Biomedical Engineering, 2019, 3:194.
23. Namkoong et al. Flexible Electronics, 2022, 6:41.
24. Liu et al. Digital Medicine, 2018, 1:19.
25. Tian et al. Advanced Functional Materials, 2017, 27:1701282.
26. Mogera et al. Science Advances, 8:1736.
27. Crawford et al. Extreme Mechanics Letters, 2018, 22:27.
28. Yu et al. Nature, 2019, 575:473.
29. Webb et al. Nature Materials, 2013, 12:938.
30. Yeo et al. Advanced Materials, 2013, 25:2773.
31. Wang et al. Advanced Functional Materials, 2022, 32:2111228.
32. Wicaksono et al. Flexible Electronics, 2020, 4:5.
33. Chung et al. Nature Medicine, 2020, 26:418.
34. Kwak et al. Advanced Materials, 2021, 33:2103974.
35. u et al. Science Advances, 9:0575.
36. Xu et al. Proceedings of the National Academy of Sciences 2020, 117:205.
37. Ha et al. Advanced Materials 2021, 33:2103320.
38. Yang et al. Nano Energy, 2022, 103:107807.
39. Ní et al. J. Mech. Behav. Biomed. Mater. 2012, 5:139.
40. Charlton et al. Plos One 2020, 15.
41. Vesnovsky et al. Modeling of Differences Between Body Core and Forehead Temperatures Measured by Infrared Thermometers, Design of Medical Devices Conference, 2017.
42. Ng et al. American Journal of Infection Control 2005, 33:227.
43. Hoffmann et al. Obesity 2012, 20:1585.

44. American Society of PeriAnesthesia Nurses-ASPAN. J Perianesth Nurs. 2001, 16:305-314.
45. Association of Surgical Technologists-AST. AST Guideline Statement for the Maintenance of Normothermia in the Patient. 2005. Perioperative static1.squarespace.com/static/Guideline_Normothermia.pdf.
46. Forbes et al. J Am Coll Surg. 2009, 209:492-504.
47. Diaz M. Hypothermia and Temperature Regulation Considerations during Anesthesia. sld.cu/galerias/pdf/sitios/anestesiologia/hypothermia.pdf, 2015.
48. Görges et al. Paediatr Anaesth. 2013, 23:1054-1061.
49. Leaper et al. Int Wound J. 2015, 12:357-362.
50. Burns et al. J Perianesth Nurs. 2009, 24:167-176.
51. Torossian A et al. Dtsch Arztebl Int. 2015, 112:166-172.
52. NICE-National Institute for Health and Care Excellence. The Management of Inadvertent Perioperative Hypothermia in Adults. 2008, nice.org.uk/guidance/cg65/chapter/Recommendations.
53. Journeaux M. Perioperative Hypothermia: Implications for Practice. Nurs Stand. 2013, 27:33-38.

What is claimed is:

1. A thermal device for monitoring core body temperature in a subject, consisting of:
   a patch made of a flexible, foldable substrate that when folded forms a top layer that is a thermal zone and a bottom layer having an adhesive disposed thereon, said patch removably attachable to the skin, said patch consisting of:
   on the thermal zone:
      an annular copper ring circumferentially disposed around a thermally conducting material and electrically isolated therefrom;
      a pair of copper semi-circular components disposed within the annular copper ring and electrically isolated therewithin; said thermally conducting material disposed beneath the pair of copper semi-circular components;
      a thermal sensing component comprising a plurality of thermal sensors disposed within the thermal zone on the top layer and operably connected thereon; and
      a first insulating material disposed in a covering relationship on the top layer of the patch;
   a second insulating material disposed in a covering relationship on the bottom layer of the patch and comprising a central opening therethrough sized to secure the thermally conducting material therein; and
   a wireless connection to communicate data acquired via the thermal sensing component to a machine learning algorithm configured to predict the core body temperature in the subject.

2. The thermal device of claim 1, wherein the thermally conducting material is a low-density polyethylene formed as a thermal plug.

3. The thermal device of claim 1, wherein the plurality of thermal sensors comprises:
   a first thermal sensor disposed between the pair of copper semi-circular components;
   a second thermal sensor disposed on the flexible, folded substrate radially beyond the edge of the annular copper ring;
   a third thermal sensor disposed on the flexible, folded substrate between the annular copper ring and the pair of copper semi-circular components or disposed on the annular copper ring; and
   a fourth thermal sensor disposed in a section of the flexible, folded substrate proximate to the first thermal sensor.

4. The thermal device of claim 1, wherein the first insulating material is a thermal insulating foam and the second insulating material on the bottom layer is a flexible insulating foam disposed to cover sections formed by the plurality of thermal sensors to define a thermal spatial gradient across the patch.

5. A system for predicting core body temperature in a subject, consisting of:
   the patch of claim 1; and
   said machine learning algorithm tangibly stored on an electronic device having at least a memory and a processor, said machine learning algorithm configured to receive input from at least a plurality of thermal sensors contained on the thermal component disposed on the patch and from at least one environmental context sensor and to output at least the predicted core body temperature.

6. The system of claim 5, wherein the at least one environmental context sensor is configured to provide contextual information.

7. The system of claim 6, wherein the input from the at least one environmental contextual sensor comprises a room temperature or an ambient air velocity or a combination thereof.

8. The system of claim 7, wherein the input from the at least one environmental contextual sensor further comprises an indication that the patch is covered or is uncovered after placement on the subject.

9. The system of claim 8, wherein the input from the at least one environmental contextual sensor further comprises at least one of the sex of the patient, a body mass index or time of a menstrual cycle.

10. A method for predicting a core body temperature of a patient in need thereof, comprising:
    a) adhering the patch in the system of claim 5 via the adhesive disposed thereon to the patient;
    b) transmitting data acquired by the plurality of thermal sensors as input into the machine learning algorithm comprising the system over a period of time;
    c) transmitting into the machine learning algorithm contextual data acquired by at least one environmental contextual sensor;
    d) analyzing the data to predict the core body temperature; and
    e) outputting the core body temperature; and
    f) repeating steps b) to e) at least once over a period of about 24 hours.

11. The method of claim 10, wherein the contextual data is ambient data comprising room temperature or ambient air velocity or is patient data comprising sex, body mass index or time of a menstrual cycle or a combination of the ambient data and the patient data.

12. The method of claim 11, wherein the contextual data further comprises a status of the patch as covered or not covered.

13. A use temperature measurement system for measuring core body temperature of a subject, consisting of:
    a patch consisting of:
       a flexible, folded substrate with a thermal zone on a top surface thereof;
       an electrically isolated annular copper ring disposed on the top surface of the flexible, folded substrate to surround the thermal zone;

a first semi-circular copper component and a second semi-circular copper component both disposed on the top surface of the flexible, folded substrate inside the electrically isolated annular copper ring and both electrically isolated therewithin;

a plurality of temperature sensors disposed within the thermal zone on the flexible, folded substrate and operably connected thereto;

a top insulator disposed over the top surface of the flexible, folded substrate;

a bottom flexible insulator formed with a central opening therethrough and disposed on a bottom surface of the flexible, folded substrate to cover sections thereon formed by the plurality of temperature sensors;

a thermal plug disposed beneath the first semi-circular copper component and the second semi-circular copper component and within the central opening through the bottom flexible insulator; and an adhesive disposed on the bottom surface of the flexible, folded substrate to removably secure to the subject; and a machine learning algorithm tangibly stored on an electronic device in wireless connection with the patch and having at least a memory and a processor, said machine learning algorithm configured to receive and analyze input data from the plurality of temperature sensors disposed on the temperature measurement device and from an environmental context sensor and to output at least the predicted core body temperature.

14. The temperature measurement system of claim 13, wherein the plurality of temperature sensors comprises:

a first temperature sensor disposed in the thermal conducting zone between the first copper semi-circle and the second copper semi-circle;

a second temperature sensor disposed on the flexible, folded substrate radially beyond the edge of the annular copper ring;

a third temperature sensor disposed on the flexible, folded substrate between the annular copper ring and the copper circle or disposed on the annular copper ring; and a fourth temperature sensor disposed in a section of the flexible, folded substrate proximate to the first thermal sensor.

15. The temperature measurement system of claim 13, wherein said thermal plug is made from a low-density polyethylene.

16. The temperature measurement system of claim 14, wherein said device is constructed for a single use of about 24 hours.

17. The temperature measurement system of claim 14, wherein the contextual data input into the machine learning algorithm is an ambient temperature, an ambient air velocity, or whether the patch is covered or is uncovered when on the subject, or is the sex of the subject, a body mass index of the subject or a time of a menstrual cycle or a combination thereof.

18. The temperature measurement system of claim 13, wherein
the top insulator is a thermal insulating foam and the bottom flexible insulator is a flexible insulating foam disposed to cover sections formed by the plurality of temperature sensors to define a thermal spatial gradient across the patch.

19. A method for predicting a core body temperature of a patient in need thereof, comprising:
a) adhering the patch comprising the system of claim 13 via the adhesive disposed thereon to the patient;
b) transmitting data acquired by the plurality of thermal sensors as input into the machine learning algorithm comprising the system over a period of time;
c) transmitting into the machine learning algorithm contextual data acquired by the environmental contextual sensor;
d) analyzing the data and the contextual data to at least predict the core body temperature;
e) outputting at least the core body temperature; and
f) repeating steps b) to e) at least once over a period of about 24 hours.

* * * * *